(12) United States Patent
Bacon et al.

(10) Patent No.: US 9,079,887 B2
(45) Date of Patent: Jul. 14, 2015

(54) ANTIVIRAL COMPOUNDS

(71) Applicant: Gilead Sciences, Inc., Foster City, CA (US)

(72) Inventors: Elizabeth M. Bacon, Burlingame, CA (US); Jeromy J. Cottell, Redwood City, CA (US); John O. Link, San Francisco, CA (US); Teresa Alejandra Trejo Martin, Union City, CA (US)

(73) Assignee: Gilead Sciences, Inc., Foster, CA (US)

( * ) Notice: Subject to any disclaimer, the term of this patent is extended or adjusted under 35 U.S.C. 154(b) by 163 days.

(21) Appl. No.: 13/828,104

(22) Filed: Mar. 14, 2013

(65) Prior Publication Data

US 2013/0309195 A1    Nov. 21, 2013

Related U.S. Application Data

(60) Provisional application No. 61/647,979, filed on May 16, 2012, provisional application No. 61/648,414, filed on May 17, 2012.

(51) Int. Cl.

| | | |
|---|---|---|
| *A61K 31/415* | (2006.01) | |
| *A61K 31/40* | (2006.01) | |
| *A61K 47/00* | (2006.01) | |
| *C07D 413/00* | (2006.01) | |
| *C07D 403/14* | (2006.01) | |
| *A61K 31/4178* | (2006.01) | |
| *A61K 31/7056* | (2006.01) | |
| *A61K 38/21* | (2006.01) | |
| *A61K 45/06* | (2006.01) | |
| *A61K 31/7072* | (2006.01) | |
| *C07D 405/14* | (2006.01) | |
| *A61K 31/7064* | (2006.01) | |
| *C07D 401/14* | (2006.01) | |

(52) U.S. Cl.
CPC .......... *C07D 403/14* (2013.01); *A61K 31/4178* (2013.01); *A61K 31/7056* (2013.01); *A61K 31/7064* (2013.01); *A61K 31/7072* (2013.01); *A61K 38/21* (2013.01); *A61K 45/06* (2013.01); *C07D 401/14* (2013.01); *C07D 405/14* (2013.01)

(58) Field of Classification Search
None
See application file for complete search history.

(56) References Cited

FOREIGN PATENT DOCUMENTS

| WO | WO 2010/111673 A1 | 9/2010 |
|---|---|---|
| WO | WO 2010/132601 A1 | 11/2010 |
| WO | WO 2010/138368 A1 | 12/2010 |
| WO | WO 2012/068234 A2 | 5/2012 |

OTHER PUBLICATIONS

Search Report from PCT/US2013/041205 dated Jul. 1, 2013.

*Primary Examiner* — Jeffrey S Lundgren
*Assistant Examiner* — Michael Schmitt

(57) ABSTRACT

The invention is related to anti-viral compounds, compositions containing such compounds, and therapeutic methods that include the administration of such compounds, as well as to processes and intermediates useful for preparing such compounds.

28 Claims, No Drawings

ANTIVIRAL COMPOUNDS

CROSS REFERENCE TO RELATED APPLICATIONS

This application claims the benefit under 35 U.S.C. 119(e) of U.S. Provisional Application Nos. 61/647,979, filed on May 16, 2012 and 61/648,414, filed on May 17, 2012, both of which are incorporated by reference in their entirety.

BACKGROUND

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

There is a need for new HCV therapeutic agents. In particular, there is a need for HCV therapeutic agents that have broad activity against HCV genotypes (e.g. genotypes 1a, 1b, 2a, 3a, 4a). There is also a particular need for agents that are less susceptible to viral resistance. Resistance mutations to inhibitors have been described for HCV NS5A for genotypes 1a and 1b in Antimicrobial Agents and Chemotherapy, September 2010, Volume 54, p. 3641-3650.

SUMMARY

In one embodiment is provided is a compound selected from:

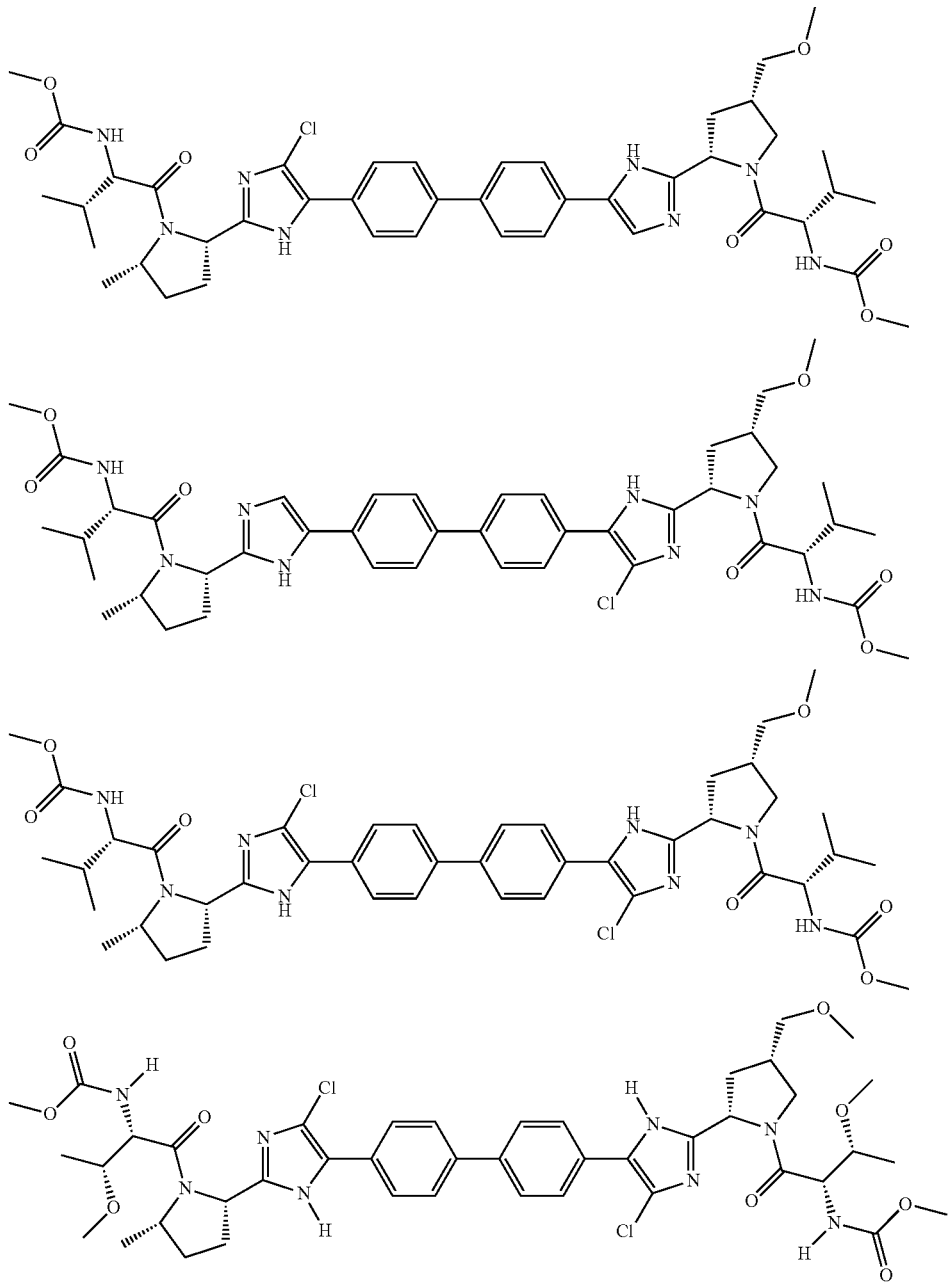

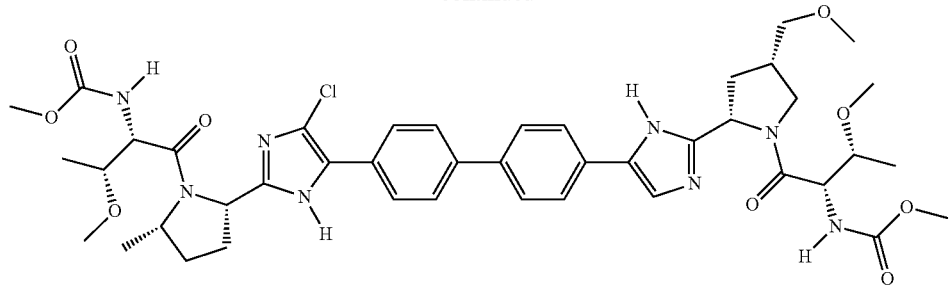
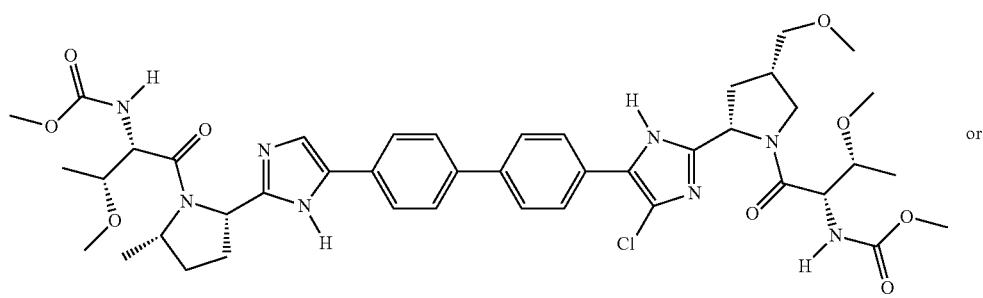
or
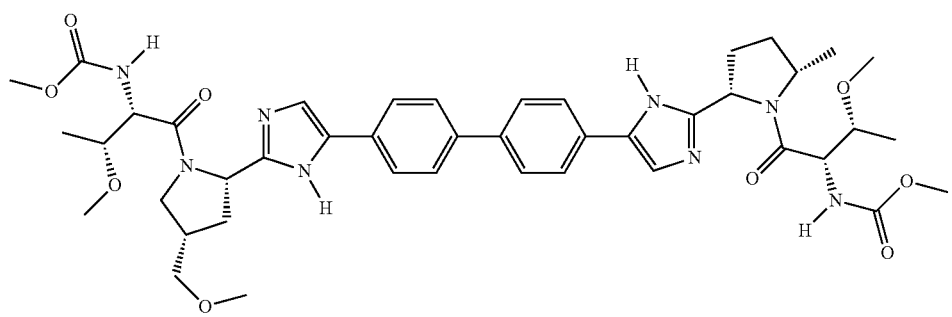
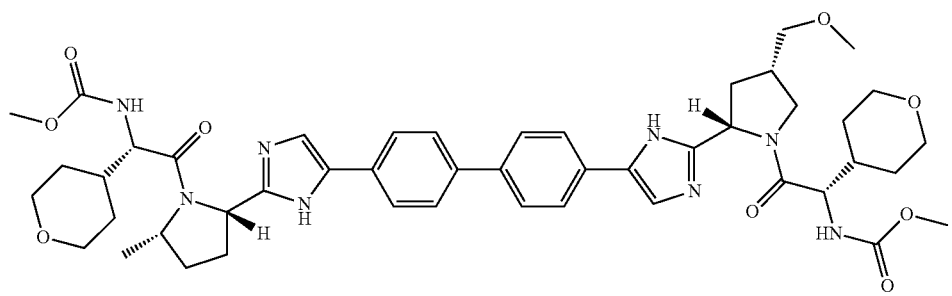
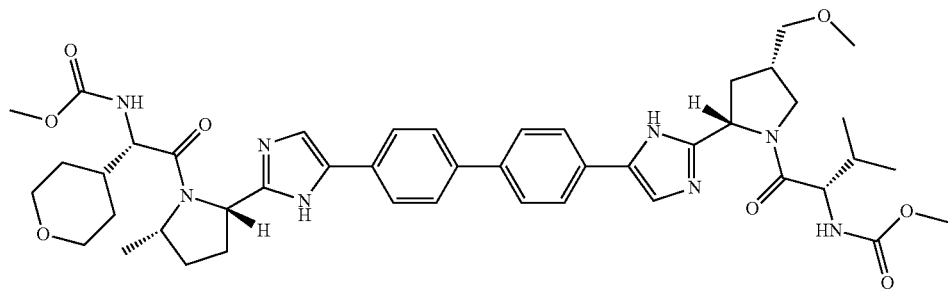

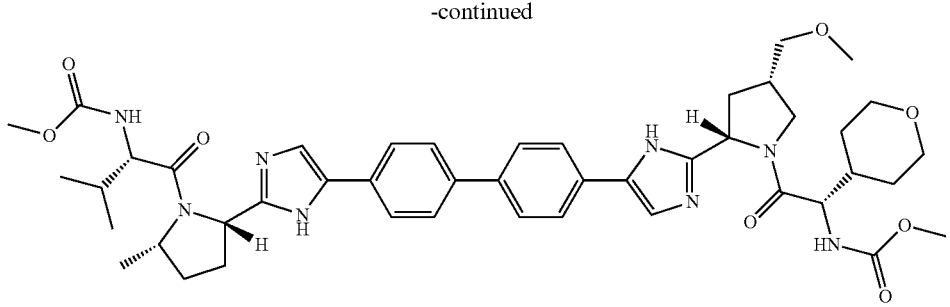

or a pharmaceutically acceptable salt or prodrug thereof.

The disclosure also provides isotopically enriched compounds that are compounds of the disclosure that comprise an enriched isotope at one or more positions in the compound.

The present disclosure also provides a pharmaceutical composition comprising a compound of the disclosure or a pharmaceutically acceptable salt or prodrug thereof and at least one pharmaceutically acceptable carrier.

The present disclosure also provides a pharmaceutical composition for use in treating hepatitis C (HCV). In one embodiment the composition comprises at least one additional therapeutic agent for treating HCV. In one embodiment, the therapeutic agent is selected from ribavirin, an NS3 protease inhibitor, a nucleoside or nucleotide inhibitor of HCV NS5B polymerase, an alpha-glucosidase 1 inhibitor, a hepatoprotectant, a non-nucleoside inhibitor of HCV polymerase, or combinations thereof. In one embodiment, the composition further comprises a nucleoside or nucleotide inhibitor of HCV NS5B polymerase. In one embodiment, the nucleoside or nucleotide inhibitor of HCV NS5B polymerase is selected from ribavirin, viramidine, levovirin, a L-nucleoside, or isatoribine.

In one embodiment, provided is a pharmaceutical composition comprising a compound as described herein and at least one nucleoside or nucleotide inhibitor of HCV NS5B polymerase, and at least one pharmaceutically acceptable carrier. In one embodiment, the composition further comprises an interferon, a pegylated interferon, ribavirin or combinations thereof. In one embodiment, the nucleoside or nucleotide inhibitor of HCV NS5B polymerase is sofosbuvir. In one embodiment, provided is a pharmaceutical composition comprising a compound as described herein and at least one NS3 protease inhibitor, and at least one pharmaceutically acceptable carrier. In one embodiment, the composition further comprises sofosbuvir.

The present disclosure also provides a pharmaceutical composition further comprising an interferon or pegylated interferon.

The present disclosure also provides a pharmaceutical composition further comprising a nucleoside analog.

The present disclosure also provides for a pharmaceutical composition wherein said nucleoside analogue is selected from ribavirin, viramidine, levovirin, an L-nucleoside, and isatoribine and said interferon is α-interferon or pegylated α-interferon.

The present disclosure also provides for a method of treating hepatitis C, said method comprising administering to a human patient a pharmaceutical composition which comprises a therapeutically effective amount of a compound of the disclosure.

The present disclosure also provides a method of inhibiting HCV, comprising administering to a mammal afflicted with a condition associated with HCV activity, an amount of a compound of the disclosure, effective to inhibit HCV.

The present disclosure also provides a compound of the disclosure for use in medical therapy (e.g. for use in inhibiting HCV activity or treating a condition associated with HCV activity), as well as the use of a compound of the disclosure for the manufacture of a medicament useful for inhibiting HCV or the treatment of a condition associated with HCV activity in a mammal.

The present disclosure also provides synthetic processes and novel intermediates disclosed herein which are useful for preparing compounds of the disclosure. Some of the compounds of the disclosure are useful to prepare other compounds of the disclosure.

In another aspect the disclosure provides a compound of the disclosure, or a pharmaceutically acceptable salt or prodrug thereof, for use in the prophylactic or therapeutic treatment of hepatitis C or a hepatitis C associated disorder.

In another aspect the disclosure provides a method of inhibiting HCV activity in a sample comprising treating the sample with a compound of the disclosure.

Compounds as described herein have been found to possess useful activity against several HCV genotypes. Additionally certain compounds of as described herein exhibit significant potency against resistant variants in, e.g., GT1.

DETAILED DESCRIPTION

Reference will now be made in detail to certain embodiments of the disclosure, examples of which are illustrated in the accompanying structures and formulas. While the disclosure will be described in conjunction with the enumerated embodiments, it will be understood that they are not intended to limit the disclosure to those embodiments. On the contrary, the disclosure is intended to cover all alternatives, modifications, and equivalents, which may be included within the scope of the present disclosure as defined by the embodiments.

Compounds

The compounds of the disclosure exclude compounds heretofore known. However, it is within the disclosure to use compounds that previously were not known to have antiviral properties for antiviral purposes (e.g. to produce an anti-viral effect in an animal). With respect to the United States, the compounds or compositions herein exclude compounds that are anticipated under 35 USC §102 or that are obvious under 35 USC §103.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as, for example, electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The disclosure includes all stereoisomers of the compounds described herein.

Prodrugs

The term "prodrug" as used herein refers to any compound that when administered to a biological system generates a compound of the disclosure that inhibits HCV activity ("the active inhibitory compound").

The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the disclosure include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the disclosure. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Protecting Groups

In the context of the present disclosure, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as, for example, the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as, for example, passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the disclosure. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as, for example, carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the disclosure may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in Protective Groups in Organic Synthesis, Theodora W. Greene (John Wiley & Sons, Inc., New York, 1991, ISBN 0-471-62301-6) ("Greene"). See also Kocienski, Philip J.; Protecting Groups (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the disclosure may have chiral centers, e.g., chiral carbon or phosphorus atoms. The compounds of the disclosure thus include all stereoisomers, including enantiomers, diastereomers, and atropisomers. In addition, the compounds of the disclosure include enriched or resolved optical isomers at any or all asymmetric, chiral atoms. In other words, the chiral centers apparent from the depictions are provided as the non-racemic or racemic mixtures. Both racemic and diastereomeric mixtures, as well as the individual optical isomers isolated or synthesized, substantially free of their enantiomeric or diastereomeric partners, are all within the scope of the disclosure. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material or through enantioselective reactions.

The compounds of the disclosure can also exist as tautomeric isomers in certain cases. Although only one tautomer may be depicted, all such forms are contemplated within the scope of the disclosure. For example, ene-amine tautomers can exist for purine, pyrimidine, imidazole, guanidine, amidine, and tetrazole systems and all their possible tautomeric forms are within the scope of the disclosure.

Salts and Hydrates

Examples of physiologically or pharmaceutically acceptable salts of the compounds of the disclosure include salts derived from an appropriate base, such as, for example, an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as, for example, acetic, benzoic, lactic, fumaric, tartaric, maleic, malonic, malic, isethionic, lactobionic and succinic acids; organic sulfonic acids, such as, for example, methanesulfonic, ethanesulfonic, benzenesulfonic and p-toluenesulfonic acids; and inorganic acids, such as, for example, hydrochloric, sulfuric, phosphoric and sulfamic acids. Physiologically acceptable salts of a compound of a hydroxy group include the anion of said compound in combination with a suitable cation such as, for example, $Na^+$ and $NX_4^+$ (wherein X is independently selected from H or a $C_1$-$C_4$ alkyl group).

For therapeutic use, salts of active ingredients of the compounds of the disclosure will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present disclosure.

Metal salts typically are prepared by reacting the metal hydroxide with a compound of this disclosure. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the disclosure in their un-ionized, as well as zwitterionic form, and combinations with stoichiometric amounts of water as in hydrates.

Also included within the scope of this disclosure are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as, for example, glycine, serine, threonine, alanine, isoleucine, or leucine.

Methods of Inhibition of HCV

Another aspect of the disclosure relates to methods of inhibiting the activity of HCV comprising the step of treating a sample suspected of containing HCV with a compound or composition of the disclosure.

The treating step of the disclosure comprises adding the compound of the disclosure to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as, for example, observation of the physiological properties of a living organism are also applicable.

Many organisms contain HCV. The compounds of this disclosure are useful in the treatment or prophylaxis of conditions associated with HCV activation in animals or in man.

However, in screening compounds capable of inhibiting HCV activity it should be kept in mind that the results of enzyme assays may not always correlate with cell culture assays. Thus, a cell based assay should typically be the primary screening tool.

Pharmaceutical Formulations

The compounds of this disclosure are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as, for example, those set forth in the Handbook of Pharmaceutical Excipients (1986). Excipients include ascorbic acid and other antioxidants, chelating agents such as, for example, EDTA, carbohydrates such as, for example, dextrin, hydroxyalkylcellulose, hydroxyalkylmethylcellulose, stearic acid and the like. The pH of the formulations ranges from about 3 to about 11, but is ordinarily about 7 to 10. Typically, the compound will be administered in a dose from 0.01 milligrams to 2 grams. In one embodiment, the dose will be from about 10 milligrams to 450 milligrams. It is contemplated that the compound may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as, for example, capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as, for example, a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as, for example, 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as, for example, propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as, for example, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as, for example, white soft paraffin and/or liquid paraffin or other mineral oils are used.

Pharmaceutical formulations according to the present disclosure comprise one or more compounds of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcellulose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as, for example, gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as, for example, 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as, for example, compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the disclosure can also be formulated to provide controlled release of the active ingredient to allow less frequent dosing or to improve the pharmacokinetic or toxicity profile of the active ingredient. Accordingly, the disclosure also provides compositions comprising one or more compounds of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the disclosure (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this disclosure is that they are orally bioavailable and can be dosed orally.

HCV Combination Therapy

In another embodiment, non-limiting examples of suitable combinations include combinations of one or more compounds of formula (I) and (A1-A4) with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, one or more compounds of the present as described herein may be combined with one or more compounds selected from the group consisting of 1) interferons, e.g., pegylated rIFN-alpha 2b (PEG-Intron®), pegylated rIFN-alpha 2a (Pegasys®), rIFN-alpha 2b (Intron® A), rIFN-alpha 2a (Roferon®-A), interferon alpha (MOR-22, OPC-18, Alfaferone®, Alfanative®, Multiferon®, subalin), interferon alfacon-1 (Infergen®), interferon alpha-n1 (Wellferon), interferon alpha-n3 (Alferon®), interferon-beta (Avonex®, DL-8234), interferon-omega (omega DUROS®, Biomed® 510), albinterferon alpha-2b (Albuferon®), IFN alpha-2b XL, BLX-883 (Locteron®), DA-3021, glycosylated interferon alpha-2b (AVI-005), PEG-Infergen, PEGylated interferon lambda-1 (PEGylated IL-29), and Belerofon®;

2) ribavirin and its analogs, e.g., ribavirin (Rebetol®, Copegus®), and taribavirin (Viramidine®);

3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, AT26893, MK5172, MK6325, and MK2748;

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, BCX-4678, valopicitabine (NM-283), MK-0608, sofosbuvir (GS-7977 (formerly PSI-7977)), VLX-135 (formerly ALS-2200), and INX-189 (now BMS986094);

7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669, PSI-7792, and GS-9190;

8) HCV NS5A inhibitors, e.g., AZD-2836 (A-831), BMS-790052, ACH-3102, ACH-2928, MK8325, MK4882, MK8742, PSI-461, IDX719, GS-5885, and A-689;
9) TLR-7 agonists, e.g., imiquimod, 852A, GS-9524, ANA-773, ANA-975 (isatoribine), AZD-8848 (DSP-3025), and SM-360320;
10) cyclophillin inhibitors, e.g., DEBIO-025, SCY-635, and NIM811;
11) HCV IRES inhibitors, e.g., MCI-067;
12) pharmacokinetic enhancers, e.g., BAS-100, SPI-452, PF-4194477, TMC-41629, GS-9350 (cobicistat), GS-9585, and roxythromycin; and
13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In yet another embodiment, the present application discloses pharmaceutical compositions comprising a compound as described herein, or a pharmaceutically acceptable salt, solvate, and/or ester thereof, in combination with at least one additional therapeutic agent, and a pharmaceutically acceptable carrier or excipient.

In another embodiment is provided a pharmaceutical composition comprising a compound as described herein and sofosbuvir and/or GS-5885 and optionally an interferon or ribavirin.

It is contemplated that additional therapeutic agents will be administered in a manner that is known in the art and the dosage may be selected by someone of skill in the art. For example, additional therapeutic agents may be administered in a dose from about 0.01 milligrams to about 2 grams per day.

Metabolites of the Compounds

Also falling within the scope of this disclosure are the in vivo metabolic products of the compounds described herein. Such products may result for example from the oxidation, reduction, hydrolysis, amidation, esterification and the like of the administered compound, primarily due to enzymatic processes. Accordingly, the disclosure includes compounds produced by a process comprising contacting a compound of this disclosure with a mammal for a period of time sufficient to yield a metabolic product thereof. Such products typically are identified by preparing a radiolabelled (e.g., $C^{14}$ or $H^3$) compound of the disclosure, administering it parenterally in a detectable dose (e.g., greater than about 0.5 mg/kg) to an animal such as, for example, rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the disclosure even if they possess no HCV-inhibitory activity of their own.

Methods for determining stability of compounds in surrogate gastrointestinal secretions are known.

Exemplary Methods of Making the Compounds

The disclosure also relates to methods of making the compositions of the disclosure. The compositions are prepared by any of the applicable techniques of organic synthesis. Many such techniques are well known in the art. However, many of the known techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., Advanced Organic Chemistry, Third Edition, (John Wiley & Sons, New York, 1985), Comprehensive Organic Synthesis. Selectivity, Strategy & Efficiency in Modern Organic Chemistry. In 9 Volumes, Barry M. Trost, Editor-in-Chief (Pergamon Press, New York, 1993 printing). Other methods suitable for preparing compounds of the disclosure are described in International Patent Application Publication Number WO 2006/020276.

A number of exemplary methods for the preparation of the compositions of the disclosure are provided in the schemes and examples below. These methods are intended to illustrate the nature of such preparations and are not intended to limit the scope of applicable methods.

Generally, the reaction conditions such as, for example, temperature, reaction time, solvents, work-up procedures, and the like, will be those common in the art for the particular reaction to be performed. The cited reference material, together with material cited therein, contains detailed descriptions of such conditions. Typically the temperatures will be $-100°$ C. to $200°$ C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about $20°$ C.), although for metal hydride reductions frequently the temperature is reduced to $0°$ C. to $-100°$ C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common Solvents can be either protic (common in equilibrating reactions) or aprotic (common in kinetically controlled reactions).

Standard synthetic techniques such as, for example, azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the Examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as, for example, activated carbon, molecular sieves, ion exchange media, or the like. Alternatively, the reagents can be acids in the case of a basic material, bases in the case of an acidic material, binding reagents such as, for example, antibodies, binding proteins, selective chelators such as, for example, crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as, for example, formation of diastereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as, for example, brucine, quinine, ephedrine, strychnine, α-methyl-β-phenylethylamine (amphetamine), and the like with asymmetric compounds bearing acidic functionality, such as, for example, carboxylic acid and sulfonic acid. The diastereomeric salts may be induced to separate by fractional crystallization or ionic chromatography. For separation of the optical isomers of amino compounds, addition of chiral carboxylic or sulfonic acids, such as, for example, camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as, for example, menthyl derivatives, followed by separation of the diastereomers and hydrolysis to yield the free, enantiomerically enriched substrate. A method of determining optical purity involves making chiral esters, such as, for example, a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as, for example, optical rotation and circular dichroism.

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the disclosure are provided herein, for example, in the Examples below. These methods are intended to illustrate the nature of such preparations and are not intended to limit the scope of applicable methods. Certain compounds of the disclosure can be used as intermediates for the preparation of other compounds of the disclosure. In the exemplary methods described herein, the fragment E-V- can also be written as R9-. PG represents a protecting group common for the given functional group that it is attached. The installation and removal of the protecting group can be accomplished using standard techniques, such as, for example, those described in Wuts, P. G. M., Greene, T. *Protective Groups in Organic Synthesis*, 4th ed.; John Wiley & Sons, Inc.: Hoboken, N.J., 2007.

In the schemes that follow, representative methods for making compounds of formula I is provided:

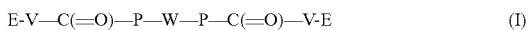   (I)

wherein:
each E is independently

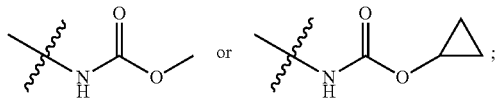

each V is independently

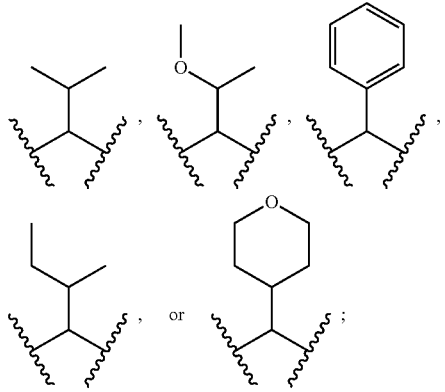

each P is independently

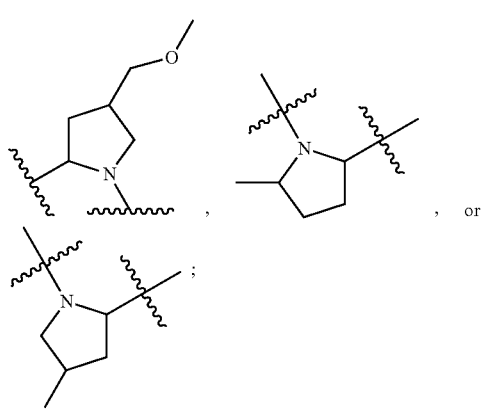

W is

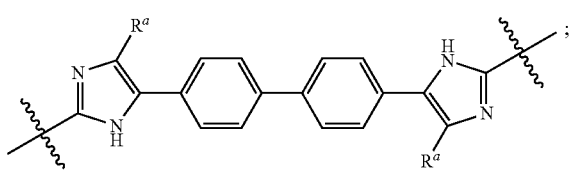

and
$R^a$ is hydrogen or chloro
or a pharmaceutically acceptable salt or prodrug thereof.

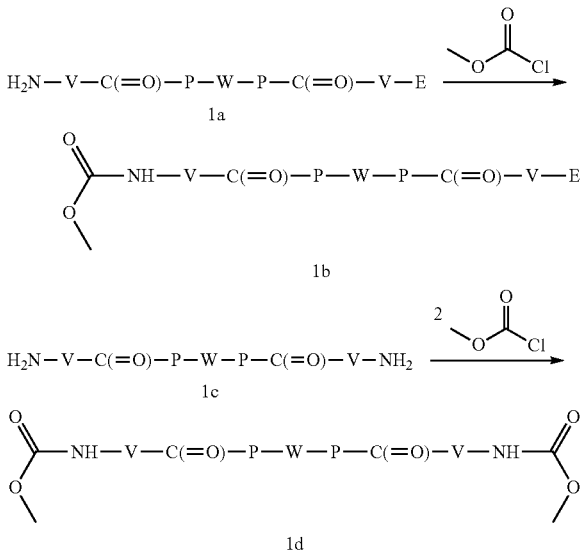

Scheme 1 shows a general synthesis of an E-V—C(=O)—P—W—P—C(=O)—V-E molecule of the disclosure wherein, for illustrative purposes, E is methoxycarbonylamino. The treatment of either 1a or 1c with one or two equivalents respectively of methyl chloroformate under basic conditions (e.g. sodium hydroxide) provides the molecule 1b or 1d.

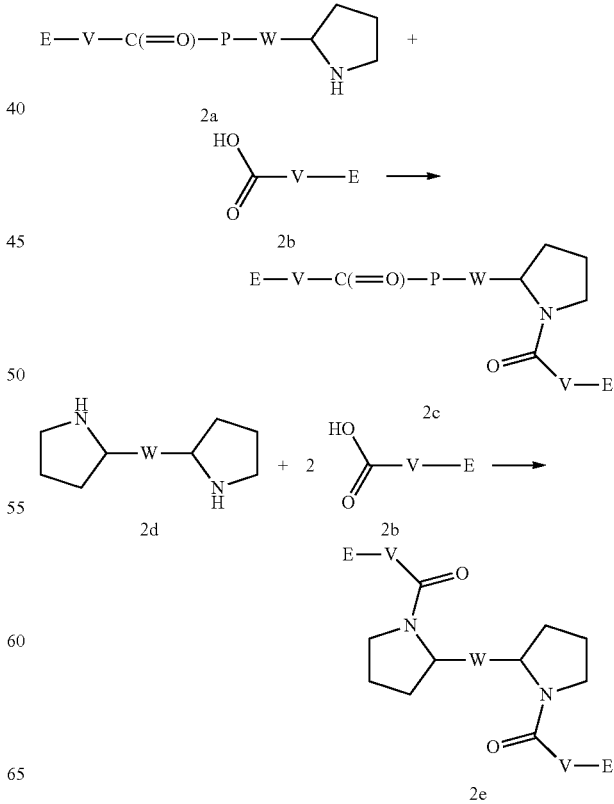

Scheme 2 shows a general synthesis of an E-V—C(=O)—P—W—P—C(=O)—V-E molecule of the disclosure wherein, for illustrative purposes, P is pyrrolidine. Coupling of amine 2a with acid 2b is accomplished using a peptide coupling reagent (e.g. HATU) to afford 2c. Alternatively, amine 2d is coupled with two equivalents of 2b under similar conditions to provide 2e.

is employed to couple a boronic ester to either an aryl- or heteroarylbromide. Boronic ester 3b is coupled with an appropriate coupling partner (e.g. 3a) using a palladium catalyst, such as Pd(PPh3)4, to afford 3c. For each transition metal mediated cross-coupling reaction, the roles of the nucleophile and electrophile can be reversed to provide the

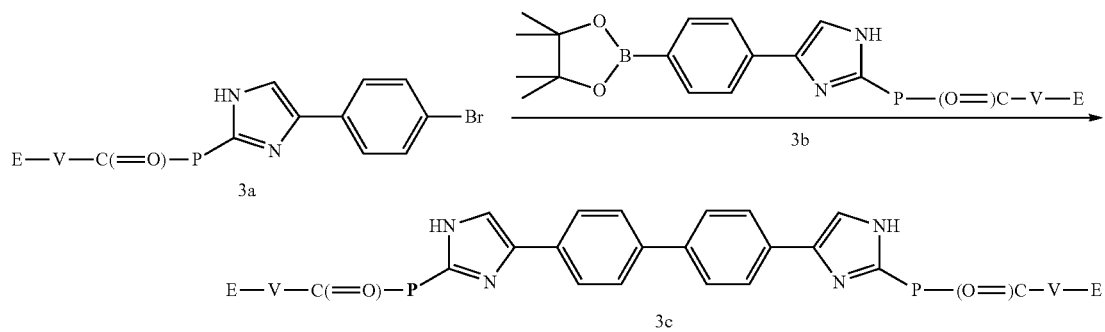

Scheme 3 shows a general synthesis of an E-V—C(=O)—P—W—P—C(=O)—V-E molecule of the invention wherein, for illustrative purposes, W is a four aromatic ring unit constructed via a transition metal mediated cross-coupling reaction. For illustrative purposes, the Suzuki reaction same coupling product. Other transition metal mediated cross couplings that enable the construction of W, but employ alternative coupling partners and reagents, include, but are not limited to, the Negishi, Kumada, Stille, Sonagashira, and Ullman couplings.

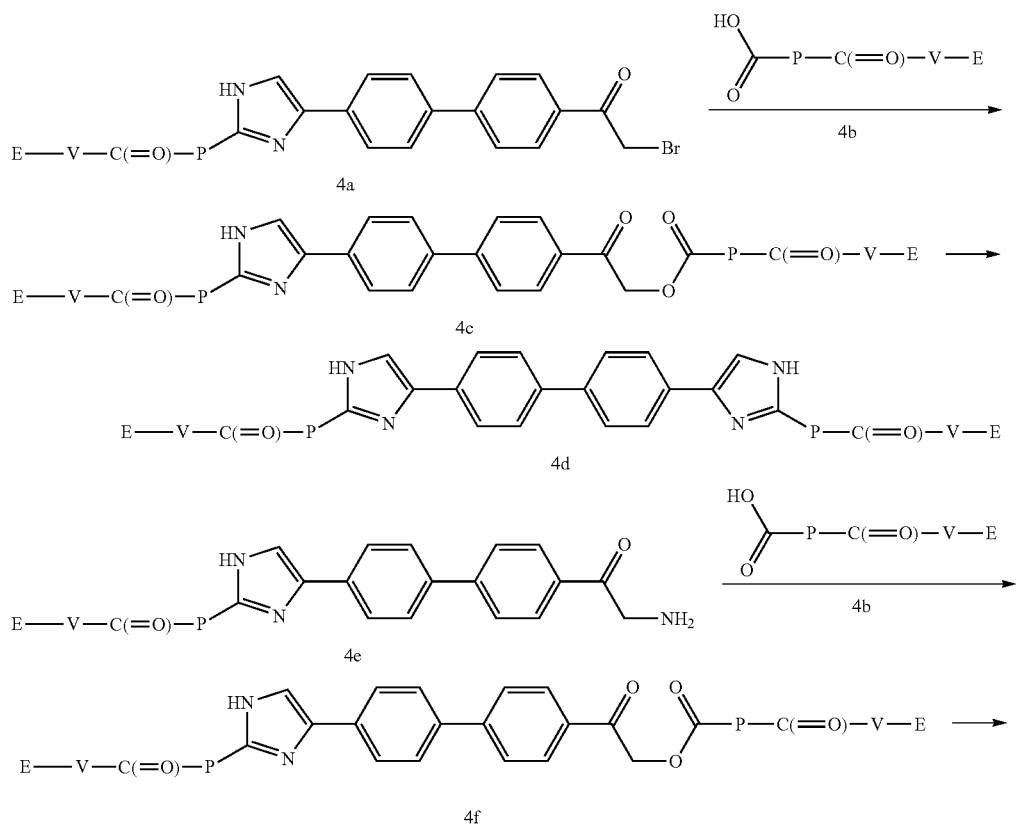

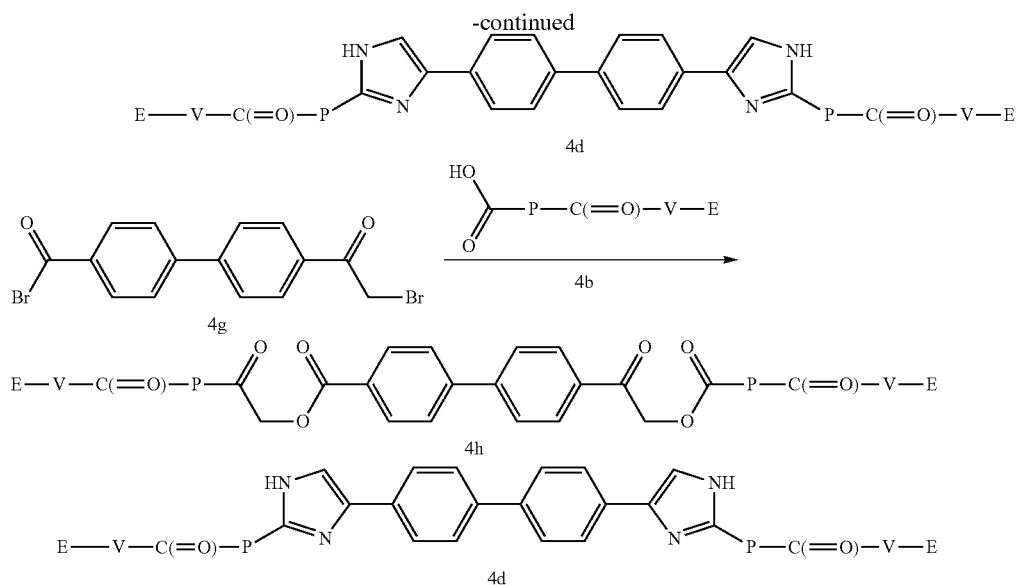

Scheme 4 shows a general synthesis of an E-V—C(=O)—P—W—P—C(=O)—V-E molecule of the invention wherein, for illustrative purposes, W is a four aromatic ring unit constructed by the formation of a substituted imidazole ring. The formation of the imidazole is accomplished by coupling the acid 4b with an α-haloketone, such as α-bromoketone 4a, under basic conditions (e.g. Et₃N) to afford 4c. Alternatively, the acid 4b is coupled with an α-aminoketone 4e, under amide formation conditions (e.g. EDC, Et₃N) to afford 4f. Reaction of 4c or 4f with an amine or amine salt (e.g. ammonium acetate) affords the imidazole containing molecule 4d.

The formation of multiple imidazoles is performed in the same manner, starting with a bis-α-haloketone such as α-bromoketone 4g, to provide molecule 4d.

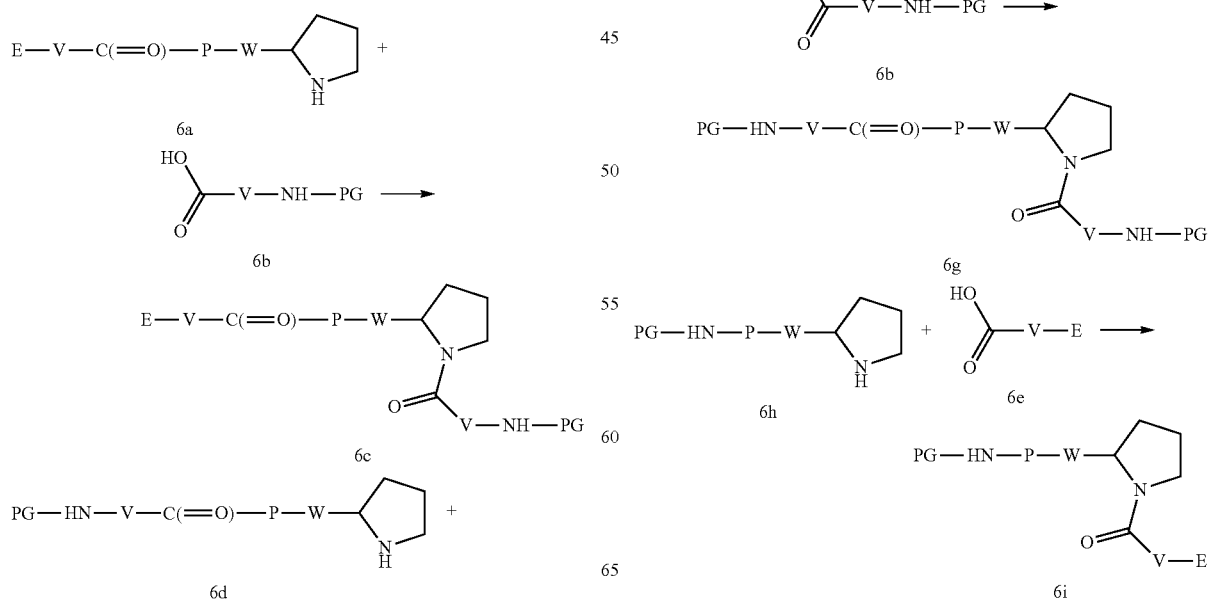

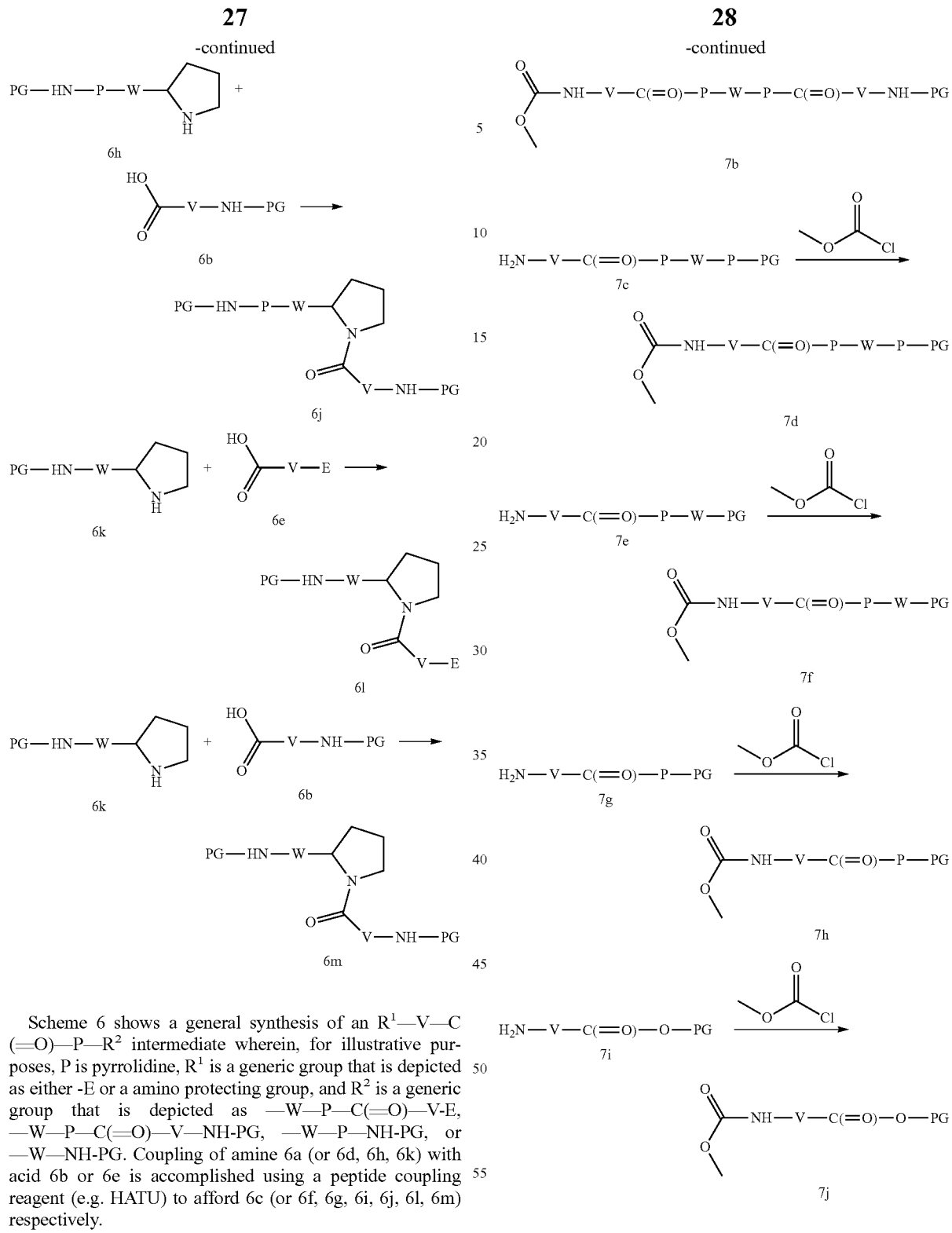

Scheme 6 shows a general synthesis of an $R^1$—V—C(=O)—P—$R^2$ intermediate wherein, for illustrative purposes, P is pyrrolidine, $R^1$ is a generic group that is depicted as either -E or a amino protecting group, and $R^2$ is a generic group that is depicted as —W—P—C(=O)—V-E, —W—P—C(=O)—V—NH-PG, —W—P—NH-PG, or —W—NH-PG. Coupling of amine 6a (or 6d, 6h, 6k) with acid 6b or 6e is accomplished using a peptide coupling reagent (e.g. HATU) to afford 6c (or 6f, 6g, 6i, 6j, 6l, 6m) respectively.

Scheme 7 shows a general synthesis of an E-V—C(=O)—$R^1$ intermediate wherein, for illustrative purposes, E is methoxycarbonylamino and R' is a generic group that is depicted as either —P—W—P—C(=O)—V—NH-PG, —P—W—P-PG, —P—W-PG, —P-PG, or —O-PG. Treatment of 7a (or 7c, 7e, 7g, 7i) with methyl chloroformate under basic conditions (e.g. sodium hydroxide) provides the molecule 7b (or 7d, 7f, 7h, 7j).

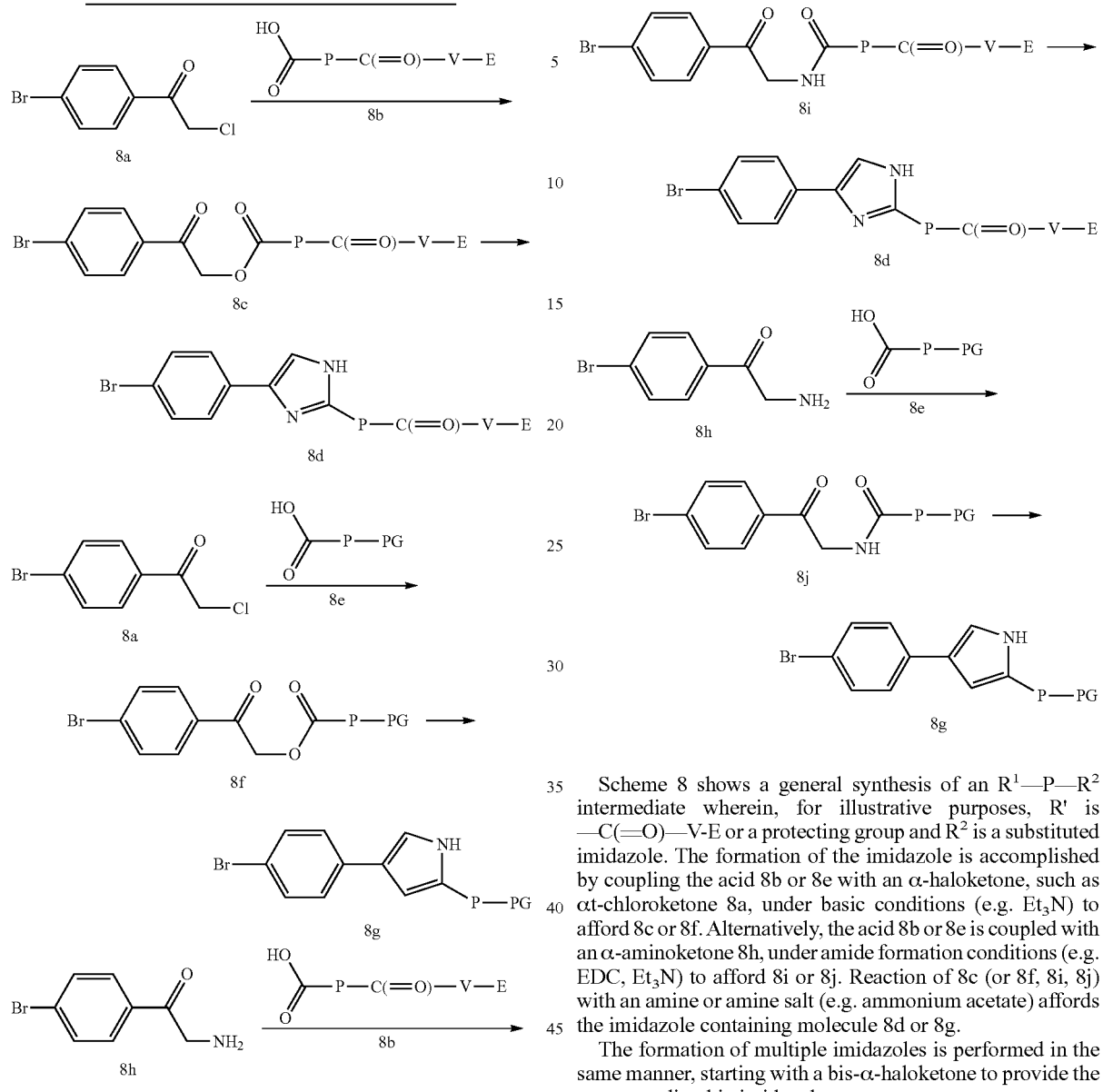

Scheme 8 shows a general synthesis of an $R^1$—P—$R^2$ intermediate wherein, for illustrative purposes, R' is —C(═O)—V-E or a protecting group and $R^2$ is a substituted imidazole. The formation of the imidazole is accomplished by coupling the acid 8b or 8e with an α-haloketone, such as αt-chloroketone 8a, under basic conditions (e.g. $Et_3N$) to afford 8c or 8f. Alternatively, the acid 8b or 8e is coupled with an α-aminoketone 8h, under amide formation conditions (e.g. EDC, $Et_3N$) to afford 8i or 8j. Reaction of 8c (or 8f, 8i, 8j) with an amine or amine salt (e.g. ammonium acetate) affords the imidazole containing molecule 8d or 8g.

The formation of multiple imidazoles is performed in the same manner, starting with a bis-α-haloketone to provide the corresponding bis-imidazole.

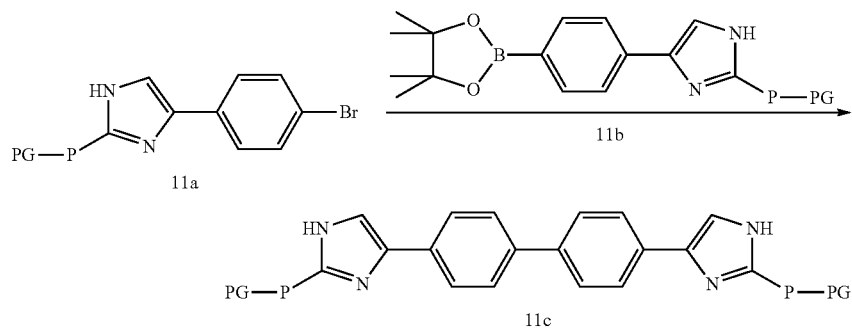

Scheme 11 shows a general synthesis of an $R^1$—P—W—P—$R^2$ intermediate of the invention wherein, for illustrative purposes, R' and $R^2$ are independent protecting groups and W is a four aromatic ring unit constructed via a transition metal mediated cross-coupling reaction. For illustrative purposes, the Suzuki reaction is employed to couple a boronic ester to either an aryl- or heteroarylbromide. Boronic ester 11b is coupled with an appropriate coupling partner (e.g. 11a) using a palladium catalyst, such as Pd(PPh3)4, to afford 11c. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, Sonagashira, and Ullman couplings.

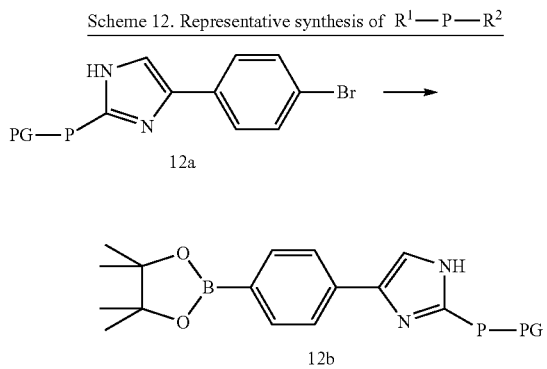

Scheme 12. Representative synthesis of $R^1$—P—$R^2$

Scheme 12 shows a general synthesis of an $R^1$—P—$R^2$ intermediate of the invention wherein, for illustrative purposes, $R^1$ is a generic group that is depicted as a protecting group and $R^2$ is a generic group that is depicted as an aryl boronic ester. A transition metal-mediated cross-coupling reaction is utilized to install the boronic ester. Treatment of the corresponding aryl bromide with a palladium catalyst, such as $PdCl_2$(dppf), and a boron source such as bis(pinacolato)diboron provides the boronic ester 12b.

The invention will now be illustrated by the following non-limiting Examples.

The disclosure will now be illustrated by the following non-limiting Examples. The following abbreviations are used throughout the specification, including the Examples.

| | |
|---|---|
| % F | % Bioavailability |
| (g) | Gas |
| ° C. | Degree Celsius |
| approx./apprx. | Approximate |
| BOC/Boc | tert-Butoxycarbonyl |
| br | Broad |
| calc'd | Calculated |
| d | Doublet |
| dba | dibenzalacetone |
| dd | Doublet of doublets |
| DMEM | Eagle's minimal essential medium |
| DMF | Dimethylformamide |
| DMSO/dmso | Dimethylsulfoxide |
| dppf | 1,1'-bis(diphenylphosphanyl) ferrocene |
| $EC_{50}$ | Half maximal effective concentration |
| EDTA | Ethylenediaminetetraacetic acid |
| ESI | Electrospray ionization |

-continued

| | |
|---|---|
| FBS | Fetal bovine serum |
| g | Gram |
| HATU | 2-(1H-7-Azabenzotriazol-1-yl)-1,1,3,3-tetramethyl uronium hexafluorophosphate Methanaminium |
| HPLC | High performance liquid chromatography |
| hr/h | Hour |
| Hz | Hertz |
| J | Coupling constant |
| L | Liter |
| LCMS | Liquid chromatography mass spectrometry |
| M | Molar |
| m | Multiplet |
| m/z | Mass to charge |
| M+ | Mass peak |
| Me | Methyl |
| mg | Milligram |
| MHz | Megahertz |
| min | Minute |
| mL | Milliliter |
| mL | Milliliter |
| mM | Millimolar |
| mm | Millimeter |
| mmol | Millimole |
| MS | Mass spectrometry |
| nm | Nanometer |
| NMR | Nuclear magnetic resonance |
| o/n | Over night |
| PBS | Phosphate buffer system |
| q | Quartet |
| quant | Quantitative |
| rt/RT | Room temperature |
| s | Singlet |
| t | Triplet |
| TFA | Trifluoroacetic acid |
| TLC | Thin layer chromatography |
| UV | Ultraviolet |
| w/w | Weight to weight |
| δ | Chemical shift |
| μL | Microliter |
| μm | Micromolar |

EXAMPLES

Example AA

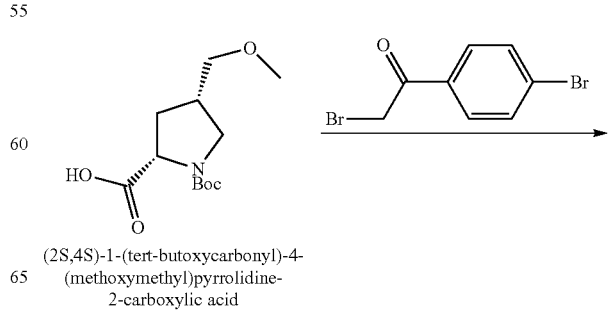

(2S,4S)-1-(tert-butoxycarbonyl)-4-(methoxymethyl)pyrrolidine-2-carboxylic acid

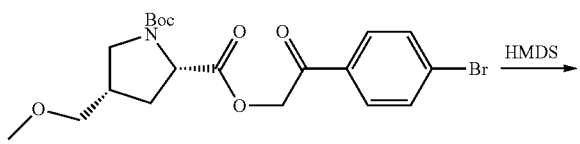

(2S,4S)-2-(2-(4-bromophenyl)-2-oxoethyl) 1-tert-butyl 4-(methoxymethyl)pyrrolidine-1,2-dicarboxylate

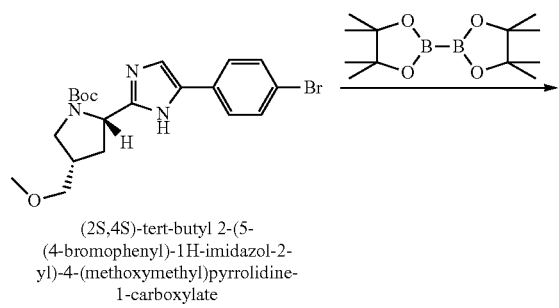

(2S,4S)-tert-butyl 2-(5-(4-bromophenyl)-1H-imidazol-2-yl)-4-(methoxymethyl)pyrrolidine-1-carboxylate

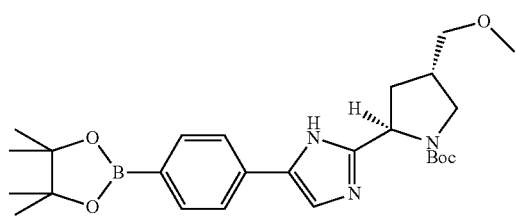

(2R,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate

(2S,4S)-2-(2-(4-bromophenyl)-2-oxoethyl) 1-tert-butyl 4-(methoxymethyl)pyrrolidine-1,2-dicarboxylate To a solution of (2S,4S)-1-(tert-butoxycarbonyl)-4-(methoxymethyl)pyrrolidine-2-carboxylic acid (2.00 g, 7.2 mmol) and 2-bromo-1-(4-bromophenyl)ethanone (2.02 g, 7.8 mmol) in MeCN (35 mL) was added triethylamine (1.1 mL, 7.9 mmol). The solution was stirred at room temperature for 24 h and diluted with EtOAc. The solution was washed aqueous HCl (1M) and brine. The aqueous layer was backextracted with EtOAc. The combined organic layers were dried over $Na_2SO_4$ and concentrated in vacuo to provide (2S,4S)-2-(2-(4-bromophenyl)-2-oxoethyl) 1-tert-butyl 4-(methoxymethyl)pyrrolidine-1,2-dicarboxylate (3.3 g, 100%).

(2S,4S)-tert-butyl 2-(5-(4-bromophenyl)-1H-imidazol-2-yl)-4-(methoxymethyl)pyrrolidine-1-carboxylate To a solution of (2S,4S)-2-(2-(4-bromophenyl)-2-oxoethyl) 1-tert-butyl 4-(methoxymethyl)pyrrolidine-1,2-dicarboxylate (3.3 g, 7.2 mmol) in toluene (50 mL) was added propionic acid (8.0 mL, 107.1 mmol) and hexamethyldisilazane (7.5 mL, 35.9 mmol). The slurry was heated to 90° C. (external temperature, oil bath) for 5 h. The solution was cooled to room temperature and diluted with EtOAc. The resulting solution was washed with ammonium hydroxide (15%). The aqueous layer was backextracted with EtOAc (5% MeOH). The combined organic layers were dried over $Na_2SO_4$ and concentrated in vacuo. The crude oil was purified by column chromatography ($SiO_2$, 10 to 60% EtOAc (5% MeOH)/Hexanes) to provide (2S,4S)-tert-butyl 2-(5-(4-bromophenyl)-1H-imidazol-2-yl)-4-(methoxymethyl)pyrrolidine-1-carboxylate (2.7 g, 87%).

(2R,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate To a solution of (2S,4S)-tert-butyl 2-(5-(4-bromophenyl)-1H-imidazol-2-yl)-4-(methoxymethyl)pyrrolidine-1-carboxylate (2.7 g, 7.0 mmol), bis(pinacolato)diboron (2.6 g, 10.5 mmol), potassium acetate (2.0 g, 20.9 mmol) in dioxane (50 mL) was added Pd(dppf)Cl$_2$ (0.32 g, 0.44 mmol). The slurry was degassed with argon for 5 min and heated to 80° C. for 5 h. The reaction was diluted with EtOAc, filtered through celite, and concentrated in vacuo. The crude oil was purified by column chromatography ($SiO_2$, 25 to 100% EtOAc (5% MeOH)/Hexanes) to provide (2R,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate (2.8 g, 84%). LCMS-ESI$^+$: calc'd for $C_{26}H_{38}BN_3O_5$: 483.29 (M$^+$). Found: 484.14 (M+H$^+$).

Example AB

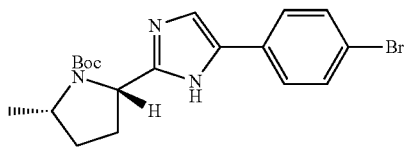

(2S,5S)-tert-butyl 2-(5-(4-bromophenyl)-1H-imidazol-2-yl)-5-methylpyrrolidine-1-carboxylate

(2S,5S)-tert-butyl 2-(5-(4-bromophenyl)-1H-imidazol-2-yl)-5-methylpyrrolidine-1-carboxylate Following Example AA substituting (2S,4S)-1-(tert-butoxycarbonyl)-4-(methoxymethyl)pyrrolidine-2-carboxylic acid with (2S,5S)-1-(tert-butoxycarbonyl)-5-methylpyrrolidine-2-carboxylic acid provided (2S,5S)-tert-butyl 2-(5-(4-bromophenyl)-1H-imidazol-2-yl)-5-methylpyrrolidine-1-carboxylate (2.2 g). LCMS-ESI$^+$: calc'd for $C_{19}H_{24}BrN_3O_2$: 405.11 (M$^+$). Found: 407.91 (M+H$^+$).

Example AC

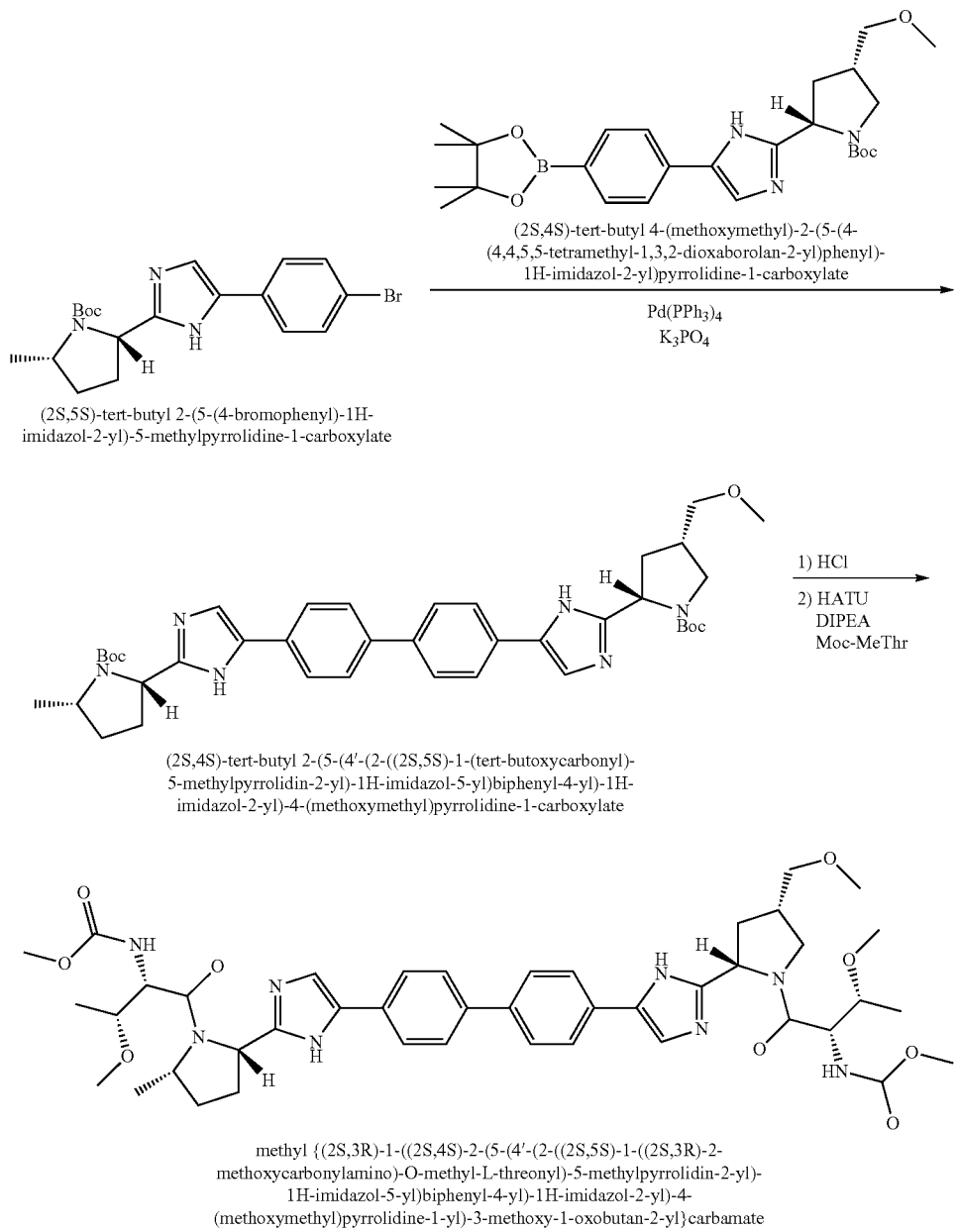

(2S,4S)-tert-butyl 2-(5-(4'-(2-((2S,5S)-1-(tert-butoxycarbonyl)-5-methylpyrrolidin-2-yl)-1H-imidazol-5-yl)biphenyl-4-yl)-1H-imidazol-2-yl)-4-(methoxymethyl)pyrrolidine-1-carboxylate To a solution of (2S,5S)-tert-butyl 2-(5-(4-bromophenyl)-1H-imidazol-2-yl)-5-methylpyrrolidine-1-carboxylate (1.0 g, 2.5 mmol) and (2S,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate (1.4 g, 2.8 mmol) in DME (12.5 mL) was added tetrakis(triphenylphosphine)-palladium (0.28 g, 0.24 mmol) and aqueous potassium phosphate (2M, 3.7 mL, 7.4 mmol). The resulting slurry was degassed with argon for 5 min and heated to 80° C. for 18 h. The reaction was cooled to room temperature and diluted with a mixture of $CH_2Cl_2$ (10% MeOH). The solution was washed with water and brine. The aqueous layer was backextracted with $CH_2Cl_2$ (10% MeOH). The combined organic layers were dried over $MgSO_4$ and concentrated in vacuo. The crude oil was purified by column chromatography ($SiO_2$, 50 to 100% EtOAc (5% MeOH)/Hexanes) to provide (2S,4S)-tert-butyl 2-(5-(4'-(2-((2S,5S)-1-(tert-butoxycarbonyl)-5-methylpyrrolidin-2-yl)-1H-imidazol-5-yl)biphenyl-4-yl)-1H-imidazol-2-yl)-4-(methoxymethyl)pyrrolidine-1-carboxylate (1.2 g, 73%). LCMS-ESI$^+$: calc'd for $C_{39}H_{50}N_6O_5$: 688.38 (M$^+$). Found: 683.51 (M+H$^+$).

methyl {(2S,3R)-1-((2S,4S)-2-(5-(4'-(2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate To a solution of (2S,4S)-tert-butyl 2-(5-(4'-(2-((2S,5S)-1-(tert-butoxycarbonyl)-5-methylpyrrolidin-2-yl)-1H-imidazol-5-yl)biphenyl-4-yl)-1H-imidazol-2-yl)-4-(methoxymethyl)pyrrolidine-1-carboxylate (0.31 g, 0.45 mmol) in a mixture of $CH_2Cl_2$ (5 mL) and MeOH (0.5 mL) was added HCl (4M in dioxanes, 4.3 mL, 17.2 mmol). The solution was heated to 40° C. for 1 hour and concentrated in vacuo. The crude intermediate was slurried in $CH_2Cl_2$ (5 mL) and (2S,3R)-3-methoxy-2-(methoxycarbonylamino)butanoic acid (Moc-MeThr) (0.18 g, 0.93 mmol), HATU (0.37 g, 0.97 mmol), and diisoproylethylamine (0.75 mL, 4.3 mmol) was added. The resulting solution was stirred at room temperature for 18 h and concentrated in vacuo. The crude product was diluted with DMF and purified by preparative HPLC (Gemini C18, 10-42% MeCN/$H_2O$ (0.1% TFA)). The desired fractions were combined and concentrated. The remaining aqueous layer was basified with saturated aqueous sodium bicarbonate. The resulting precipitate was filtered, washed with water, and dried in vacuo to provide methyl {(2S,4S)-2-(5-(4'-(2-((2S,5S)-1-((2S,3R)-2-(methoxycarbonylamino)-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate (0.22 g, 58%).

LCMS-ESI$^+$: calc'd for $C_{43}H_{56}N_8O_9$: 828.42 (M$^+$). Found: 829.77 (M+H$^+$). $^1$H NMR (400 MHz, cd3od) δ (mixture of rotomers) 7.91-7.51 (m, 8H), 7.48-7.20 (m, 2H), 5.54 (s, 1H), 5.20-4.98 (m, 2H), 4.74-4.63 (m, 1H), 4.41 (d, 1H), 4.33 (s, 1H), 4.28-4.11 (m, 2H), 3.62 (d, 5H), 3.52 (m, 4H), 3.39-3.32 (m, 4H), 3.22 (s, 3H), 2.74-2.54 (m, 2H), 2.54-2.41 (m, 2H), 2.41-1.83 (m, 6H), 1.54 (s, 1H), 1.47 (d, 2H), 1.31-1.15 (m, 3H), 1.12 (d, 4H).

Example AD-AF

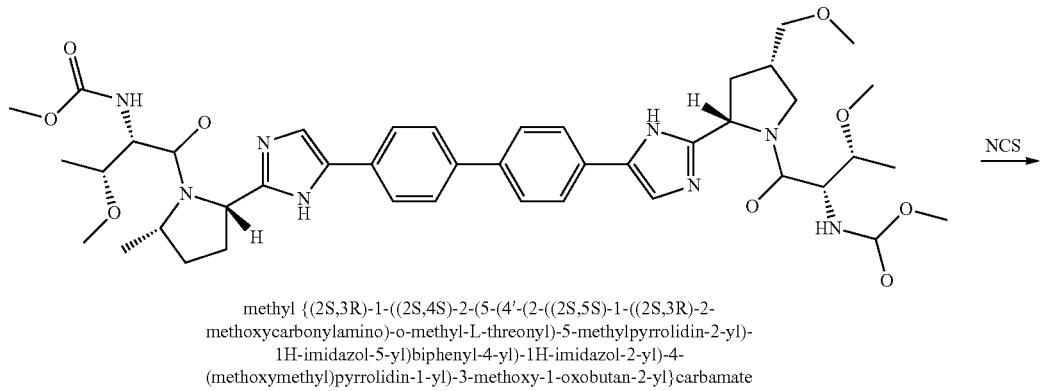

methyl {(2S,3R)-1-((2S,4S)-2-(5-(4'-(2-((2S,5S)-1-((2S,3R)-2-methoxycarbonylamino)-o-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate

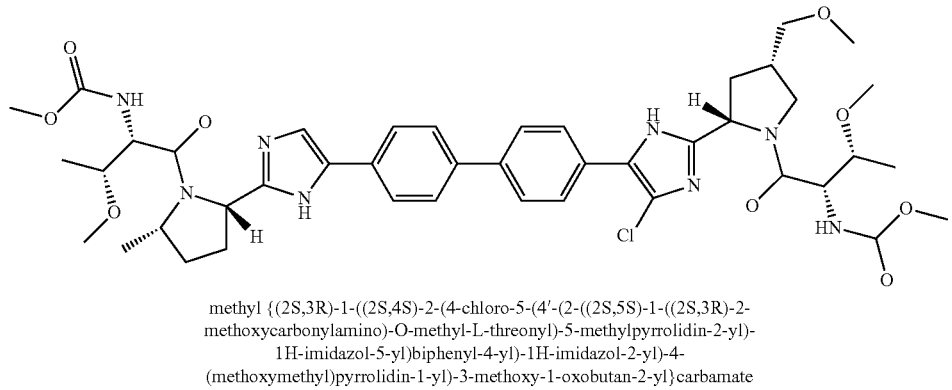

methyl {(2S,3R)-1-((2S,4S)-2-(4-chloro-5-(4'-(2-((2S,5S)-1-((2S,3R)-2-methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate -continued

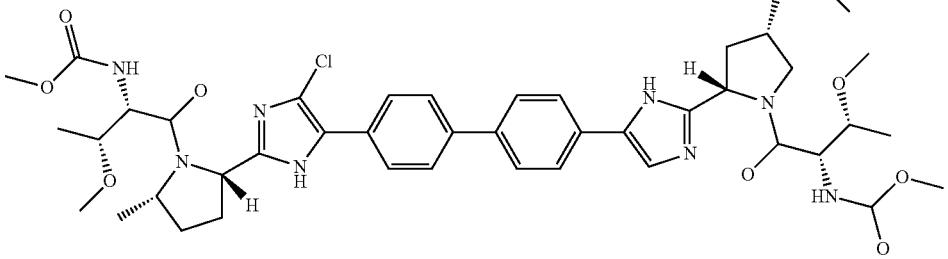

methyl {(2S,3R)-1-((2S,4S)-2-(5-(4'-(4-chloro-2-((2S,5S)-1-((2S,3R)-2-
methoxycarbonylamino)-O-methyl-L-threonyl)-5-methylpyrrolidin-2-yl)-
1H-imidazol-5-yl)biphenyl-4-yl)-1H-imidazol-2-yl)-4-
(methoxymethyl)pyrrolidin-1-yl)-3-methoxy-1-oxobutan-2-yl}carbamate

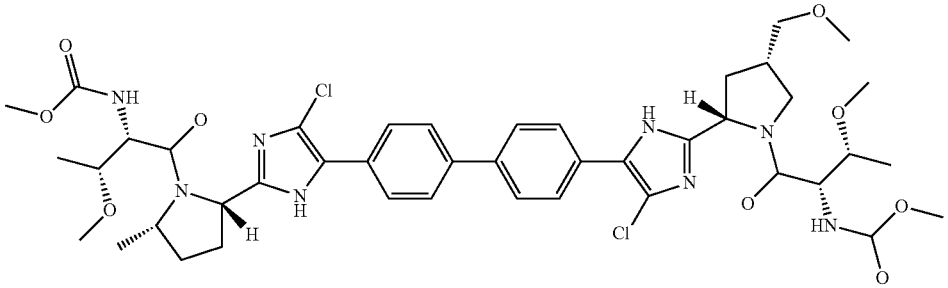

methyl {(2S,3R)-1-((2S,4S)-2-(4-chloro-5-(4'-(4-chloro-2-((2S,5S)-1-((2S,3R)-2-
methoxycarbonylamino)-O-methyl-L-threonyl)-5-methylpyrrolidin-2-yl)-
1H-imidazol-5-yl)biphenyl-4-yl)-1H-imidazol-2-yl)-4-
(methoxymethyl)pyrrolidin-1-yl)-3-methoxy-1-oxobutan-2-yl}carbamate methyl {(2S,3R)-1-(2S,4S)-2-(4-chloro-5-(4'-(2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate; methyl {(2S,3R)-1-((2S,4S)-2-(5-(4'-(4-chloro-2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate; methyl {(2S,3R)-1-((2S,4S)-2-(4-chloro-5-(4'-(4-chloro-2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate To a solution of methyl {(2S,3R)-1-((2S,4S)-2-(5-(4'-(2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate (0.12 g, 0.15 mmol) in DMF (1.5 mL) was added N-chlorosuccinimide (0.05 g, 0.38 mmol). The resulting solution was heated to 45° C. for 3 h and cooled to room temperature. The reaction solution was purified by preparative HPLC (Gemini C18, 20-75% MeCN/H$_2$O (0.1% TFA)). The desired fractions were combined and lyophilized to provide methyl {(2S,3R)-1-((2S,4S)-2-(4-chloro-5-(4'-(2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate (0.006 g, 5%).

LCMS-ESI$^+$: calc'd for $C_{43}H_{55}ClN_8O_9$: 862.38 (M$^+$). Found: 864.27 (M+H$^+$). $^1$H NMR (400 MHz, cd$_3$od) δ (mixture of rotomers) 7.88-7.63 (m, 9H), 5.83 (s, 1H), 5.14-5.03 (m, 1H), 5.02-4.91 (m, 1H), 4.66 (s, 1H), 4.35-4.25 (m, 2H), 4.19-4.06 (m, 2H), 3.65-3.51 (m, 7H), 3.51-3.39 (m, 4H), 3.28 (d, 3H), 3.16 (s, 3H), 2.64-2.33 (m, 5H), 2.23 (s, 3H), 1.90 (d, 3H), 1.44 (d, 3H), 1.23 (s, 1H), 1.12 (s, 1H), 1.04 (dd, 5H).

methyl {(2S,3R)-1-((2S,4S)-2-(5-(4'-(4-chloro-2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate (0.010 g, 8%). LCMS-ESI$^+$: calc'd for $C_{43}H_{55}ClN_8O_9$: 862.38 (M$^+$). Found: 863.96 (M+H$^+$). $^1$H NMR (400 MHz, cd3od) δ (mixture of rotomers) 7.96 (d, 1H), 7.88 (s, 1H), 7.86-7.72 (m, 7H), 5.54 (s, 1H), 5.29-5.19 (m, 1H), 5.04-4.93 (m, 1H), 4.71-4.65 (m, 1H), 4.50 (d, 1H), 4.46 (d, 1H), 4.35-4.13 (m, 3H), 3.73-3.61 (m, 7H), 3.61-3.48 (m, 4H), 3.38 (s, 3H), 3.35 (s, 2H), 2.84-2.55 (m, 4H), 2.35 (s, 3H), 2.01 (dd, 5H), 1.49 (d, 2H), 1.23-1.16 (m, 3H), 1.09 (dd, 4H).

methyl {(2S,3R)-1-((2S,4S)-2-(4-chloro-5-(4'-(4-chloro-2-((2S,5S)-1-((2S,3R)-2-(methoxycarbonylamino)-O-methyl-L-threonyl)-5-methylpyrrolidin-2-yl)-1H-imidazol-5-yl)biphenyl-4-yl)-1H-imidazol-2-yl)-4-(methoxymethyl)pyrrolidin-1-yl)-3-methoxy-1-oxobutan-2-yl}carbamate (0.05 g, 39%). LCMS-ESI$^+$: calc'd for $C_{43}H_{55}Cl_2N_8O_9$: 896.34 (M$^+$). Found: 898.56 (M+H$^+$).

Example AG-AI

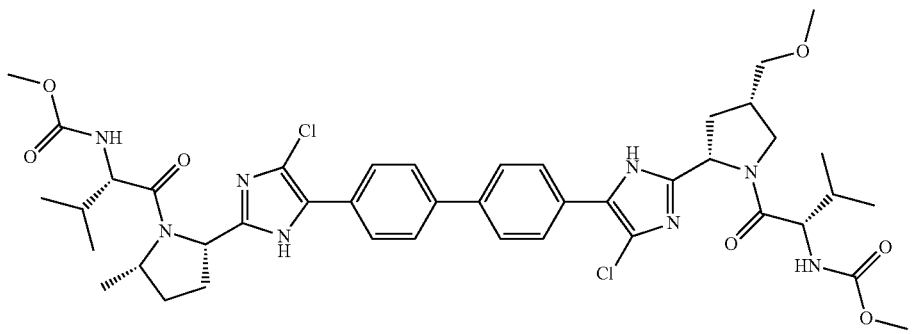

methyl (S)-1-((2S,5S)-2-(4-chloro-5-(4'-(4-chloro-2-((2S,4S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate

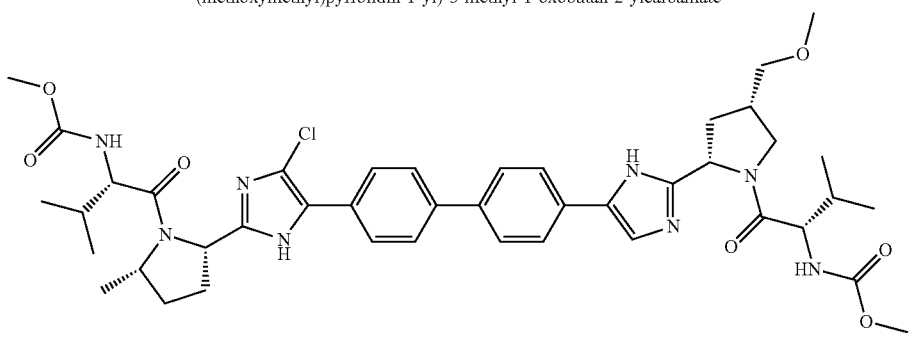

methyl (S)-1-((2S,5S)-2-(5-(4'-(4-chloro-2-((2S,4S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate

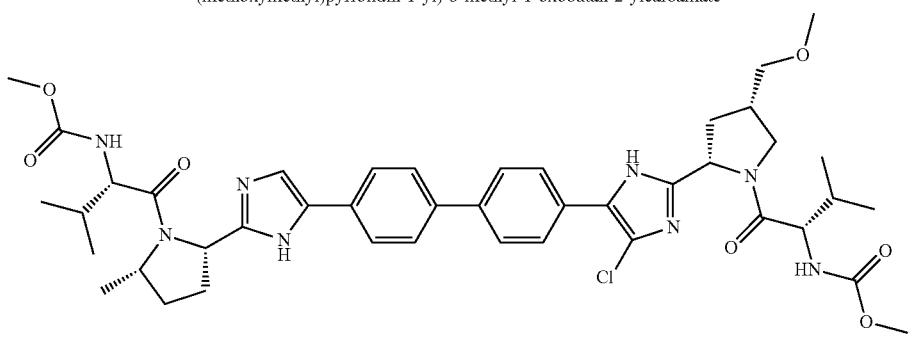

methyl (S)-1-((2S,5S)-2-(4-chloro-5-(4'-(2-((2S,4S)-1-((S)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate Methyl (S)-1-((2S,4S)-2-(4-chloro-5-(4'-(4-chloro-2-((2S,4S)-1-((R)-2-(methoxy carbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate; methyl (S)-1-((2S,4S)-2-(5-(4'-(4-chloro-2-((2S,4S)-1-((R)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate and methyl (S)-1-((2S,4S)-2-(4-chloro-5-(4'-(2-((2S,4S)-1-((R)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate were synthesized in a similar manner as example AD substituting (2S,3R)-3-methoxy-2-(methoxycarbonyl amino)butanoic acid with (S)-2-(methoxycarbonylamino)-3-methylbutanoic acid.

Methyl (S)-1-((2S,4S)-2-(4-chloro-5-(4'-(4-chloro-2-((2S,4S)-1-((R)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate. ¹H NMR (400 MHz, dmso) δ 7.98-7.67 (m, 8H), 7.58-7.38 (m, 1H), 7.23 (d, 1H), 4.88 (m, 3H), 4.74-4.53 (m, 2H), 4.22-3.70 (m, 5H), 3.58-3.48 (m, 6H), 3.47-3.33 (m, 3H), 2.38-2.07 (m, 4H), 2.04-1.68 (m, 6H), 1.38 (d, 2H), 1.10 (d, 1H), 0.95-0.70 (m, 12H). MS (ESI) m/z 866.46 [M+H]⁺.

Methyl (S)-1-((2S,4S)-2-(5-(4'-(4-chloro-2-((2S,4S)-1-((R)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate.

¹H NMR (400 MHz, dmso) δ 12.88-12.03 (m, 1H), 7.82 (m, 6H), 7.65-7.40 (m, 2H), 7.22 (d, 1H), 4.93 (d, 2H), 4.62 (s, 1H), 4.17-3.97 (m, 3H), 3.85 (m, 2H), 3.49 (m, 10H), 2.34 (s, 5H), 2.02-1.68 (m, 5H), 1.44 (d, 2H), 1.15 (t, 3H), 0.94-0.66 (m, 12H). MS (ESI) m/z 832.20 [M+H]⁺.

Methyl (S)-1-((2S,4S)-2-(4-chloro-5-(4'-(2-((2S,4S)-1-((R)-2-(methoxycarbonylamino)-3-methylbutanoyl)-5-methylpyrrolidin-2-yl)-1H-imidazol-5-yl)biphenyl-4-yl)-1H-imidazol-2-yl)-4-(methoxymethyl)pyrrolidin-1-yl)-3-methyl-1-oxobutan-2-ylcarbamate. ¹H NMR (400 MHz, dmso) δ 12.68 (s, 1H), 8.11 (s, 1H), 7.86 (m, 7H), 7.49 (d, 1H), 7.30 (d, 1H), 5.05 (s, 1H), 4.89 (s, 1H), 4.64 (s, 1H), 4.09 (d, 3H), 3.84 (d, 1H), 3.66-3.34 (m, 13H), 2.63 (s, 1H), 2.21 (d, 3H), 2.03-1.69 (m, 5H), 1.38 (d, 2H), 1.22-1.04 (m, 2H), 0.95-0.66 (m, 11H). MS (ESI) m/z 832.17 [M+H]⁺.

tic acid for (2S,3R)-3-methoxy-2-(methoxycarbonylamino)butanoic acid (0.144 g). ¹H NMR (400 MHz, Methanol-d₄) δ 7.95-7.53 (m, 11H), 7.43-7.17 (m, 3H), 5.06 (dd, 2H), 4.37-4.09 (m, 4H), 4.00-3.77 (m, 5H), 3.63 (s, 5H), 3.58-3.45 (m, 3H), 3.36 (s, 4H), 2.73-2.39 (m, 4H), 2.38-1.80 (m, 5H), 1.72 (d, J=13.1 Hz, 1H), 1.66-1.02 (m, 13H). MS (ESI) m/z 881.91 [M+H]⁺.

Example AK

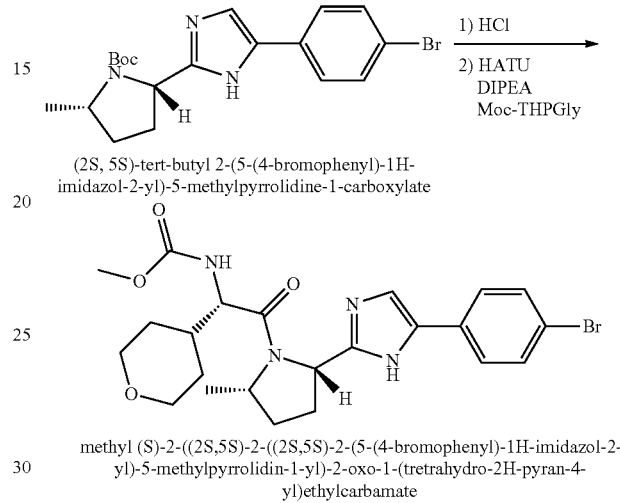

(2S, 5S)-tert-butyl 2-(5-(4-bromophenyl)-1H-imidazol-2-yl)-5-methylpyrrolidine-1-carboxylate methyl (S)-2-((2S,5S)-2-((2S,5S)-2-(5-(4-bromophenyl)-1H-imidazol-2-yl)-5-methylpyrrolidin-1-yl)-2-oxo-1-(tretrahydro-2H-pyran-4-yl)ethylcarbamate Example AJ

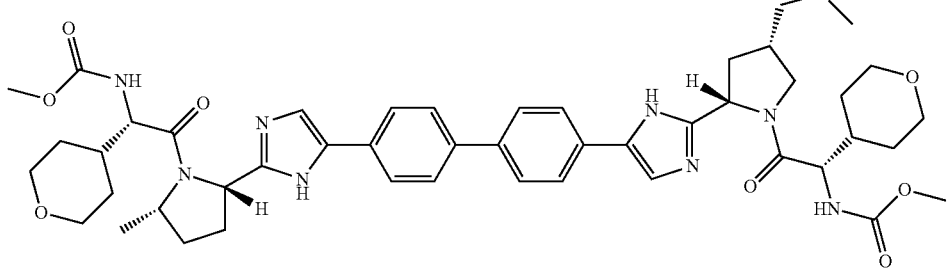

methyl [(1S)-2-{(2S,5S)-2-[5-(4'-{2-[(2S,4S)-1-[(2S)-2-[(methoxycarbonyl)amino]-2-(tetrahydro-2H-pyran-4-yl)acetyl]-4-(methoxymethyl)pyrrolidin-2-yl]-1H-imidazol-5-yl}biphenyl-4-yl)-1H-imidazol-2-yl]-5-methylpyrrolidin-1-yl}-2-oxo-1-(tetrahydro-2H-pyran-4-yl)ethyl]carbamate Methyl [(1S)-2-{(2S,5S)-2-[5-(4'-{2-[(2S,4S)-1-[(2S)-2-[(methoxycarbonyl)amino]-2-(tetrahydro-2H-pyran-4-yl)acetyl]-4-(methoxymethyl)pyrrolidin-2-yl]-1H-imidazol-5-yl}biphenyl-4-yl)-1H-imidazol-2-yl]-5-methylpyrrolidin-1-yl}-2-oxo-1-(tetrahydro-2H-pyran-4-yl)ethyl]carbamate Methyl [(1S)-2-{(2S,5S)-2-[5-(4'-{2-[(2S,4S)-1-[(2S)-2-[(methoxycarbonyl)amino]-2-(tetrahydro-2H-pyran-4-yl)acetyl]-4-(methoxymethyl)pyrrolidin-2-yl]-1H-imidazol-5-yl}biphenyl-4-yl)-1H-imidazol-2-yl]-5-methylpyrrolidin-1-yl}-2-oxo-1-(tetrahydro-2H-pyran-4-yl)ethyl]carbamate was prepared following Example AC substituting (S)-2-(methoxycarbonylamino)-2-(tetrahydro-2H-pyran-4-yl)ace- Methyl (S)-2-((2S,5S)-2-(5-(4-bromophenyl)-1H-imidazol-2-yl)-5-methylpyrrolidin-1-yl)-2-oxo-1-(tetrahydro-2H-pyran-4-yl)ethylcarbamate To a solution of (2S,5S)-tert-butyl 2-(5-(4-bromophenyl)-1H-imidazol-2-yl)-5-methylpyrrolidine-1-carboxylate (0.50 g, 1.23 mmol) in a mixture of CH₂CL₂ (10 mL) and methanol (1.0 mL) was added HCl (4M in dioxane, 6.00 mL, 24 mmol). The solution was stirred at 40° C. for 1 h, cooled to room temperature and concentrated to dryness. The crude solid was suspended in CH₂CL₂ (10 mL), followed by the addition of (S)-2-(methoxycarbonylamino)-2-(tetrahydro-2H-pyran-4-yl)acetic acid (0.298 g, 1.37 mmol), HATU (0.562 g, 1.48 mmol) and DIPEA (0.60 mL, 3.44 mmol). The resulting solution was stirred at room temperature for 18 h. The solution was diluted with CH2CL2 and washed with a mixture of sodium bicarbonate (aqueous, sat) and brine. The aqueous layer was back-extracted with CH2CL2. The combined organic layers were dried over Na2SO4 and concentrated to provide a crude oil. Purification by column chromatography (SiO2, 10-100% EtOAc (10% MeOH)/Hexanes) provided methyl (S)-2-((2S,5S)-2-(5-(4-bromophenyl)-1H-imidazol-2-yl)-5-methylpyrrolidin-1-yl)-2-oxo-1-(tetrahydro-2H-pyran-4-yl)ethylcarbamate (0.614 g, 99%). MS (ESI) m/z 505.844 [M+H]+.

Example AL

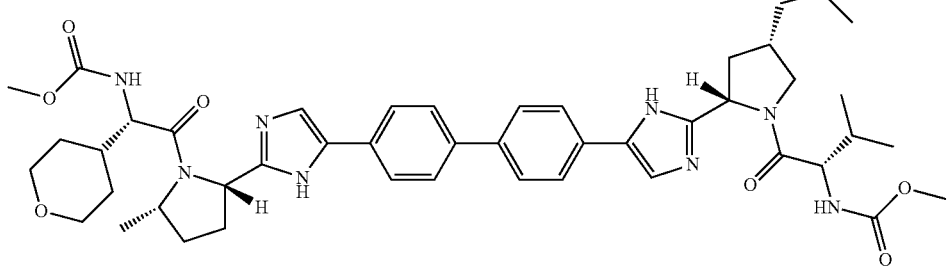

methyl {(2S)-1-[(2S,4S)-2-{5-[4'-(2-{(2S,5S)-1-[(2S)-2-[(methoxycarbonyl)amino]-2-(tetrahydro-2H-pyran-4-yl)acetyl]-5-methylpyrrolidin-2-yl}-1H-imidazol-5-yl)biphenyl-4-yl]-1H-imidazol-2-yl}-4-(methoxymethyl)pyrrolidin-1-yl]-3-methyl-1-oxobutan-2-yl}carbamate

Methyl {(2S)-1-[(2S,4S)-2-{5-[4'-(2-{(2S,5S)-1-[(2S)-2-[(methoxycarbonyl)amino]-2-(tetrahydro-2H-pyran-4-yl)acetyl]-5-methylpyrrolidin-2-yl}-1H-imidazol-5-yl)biphenyl-4-yl]-1H-imidazol-2-yl}-4-(methoxymethyl)pyrrolidin-1-yl]-3-methyl-1-oxobutan-2-yl}carbamate Methyl {(2S)-1-[(2S,4S)-2-{5-[4'-(2-{(2S,5S)-1-[(2S)-2-[(methoxycarbonyl)amino]-2-(tetrahydro-2H-pyran-4-yl)acetyl]-5-methylpyrrolidin-2-yl}-1H-imidazol-5-yl)biphenyl-4-yl]-1H-imidazol-2-yl}-4-(methoxymethyl)pyrrolidin-1-yl]-3-methyl-1-oxobutan-2-yl}carbamate was prepared following Example AC, substituting methyl (S)-2-((2S,5S)-2-(5-(4-bromophenyl)-1H-imidazol-2-yl)-5-methylpyrrolidin-1-yl)-2-oxo-1-(tetrahydro-2H-pyran-4-yl)ethylcarbamate for (2S,5S)-tert-butyl 2-(5-(4-bromophenyl)-1H-imidazol-2-yl)-5-methylpyrrolidine-1-carboxylate and (S)-2-(methoxycarbonylamino)-2-(tetrahydro-2H-pyran-4-yl) acetic acid for (2S,3R)-3-methoxy-2-(methoxycarbonylamino)butanoic acid (0.150 g). 1H NMR (400 MHz, Methanol-d4) δ 7.89-7.55 (m, 9H), 7.42-7.24 (m, 2H), 5.16-4.98 (m, 2H), 4.56 (s, 1H), 4.35-4.08 (m, 3H), 3.93 (ddd, 2H), 3.82 (dt, 1H), 3.67 (s, 2H), 3.64 (s, 2H), 3.63 (s, 3H), 3.60-3.44 (m, 3H), 3.36 (s, 4H), 3.25-3.13 (m, 1H), 2.78-2.36 (m, 3H), 2.37-1.81 (m, 7H), 1.72 (d, 1H), 1.50 (d, 2H), 1.42-1.09 (m, 3H), 0.90 (d, 4H), 0.84 (d, 3H). MS (ESI) m/z 839.79 [M+H]+.

Example AM

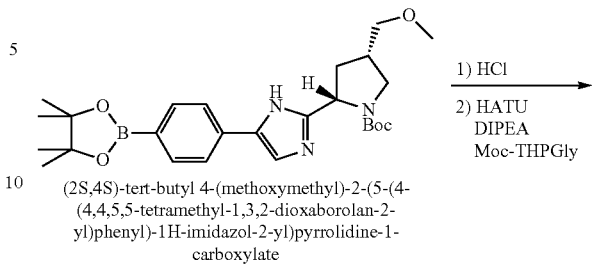

(2S,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate

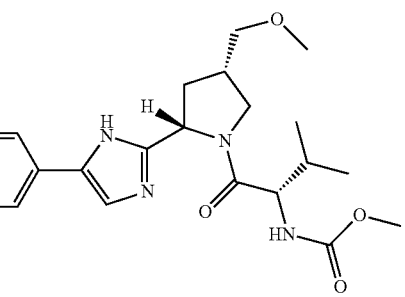

-continued

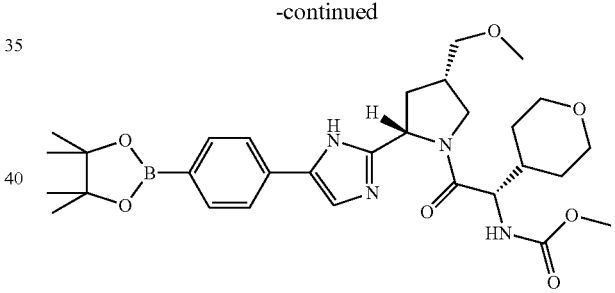

methyl (S)-2-((2S,4S)-4-(methoxymethyl)-2-(5-(4-(4,4,5,5-tetramethyl-1,3,2-dioxaborolan-2-yl)-1H-imidazol-2-yl)pyrrolidin-1-yl)-2-oxo-1-(tretrahydro-2H-pyran-4-yl)ethylcarbamate

Methyl (S)-2-((2S,4S)-4-(methoxymethyl)-2-(5-(4-(4,4,5,5-tetramethyl-1,3,2-dioxaborolan-2-yl)phenyl)-1H-imidazol-2-yl)pyrrolidin-1-yl)-2-oxo-1-(tetrahydro-2H-pyran-4-yl)ethylcarbamate To a solution of (2S,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate (0.50 g, 1.03 mmol) in a mixture of CH2Cl2 (10 mL) and methanol (1.0 mL) was added HCl (4M in dioxane, 6.00 mL, 24 mmol). The solution was stirred at 40° C. for 1 h, cooled to room temperature and concentrated to dryness. The crude solid was suspended in CH2CL2 (10 mL), followed by the addition of (S)-2-(methoxycarbonylamino)-2-(tetrahydro-2H-pyran-4-yl)acetic acid (0.260 g, 1.20 mmol), HATU (0.475 g, 1.25 mmol) and DIPEA (0.60 mL, 3.44 mmol). The resulting solution was stirred at room temperature for 18 h. The solution was diluted with CH2CL2 and washed with a mixture of sodium bicarbonate (aqueous, sat) and brine. The aqueous layer was back-extracted with CH2CL2. The combined organic layers were dried over Na2SO4 and concentrated to provide a crude oil. Purification by column chromatography (SiO2, 10-100% EtOAc (10% MeOH)/Hexanes) provided methyl (S)-2-((2S,4S)-4-(methoxymethyl)-2-(5-(4-(4,4,5,5-tetramethyl-1,3,2-dioxaborolan-2-yl)phenyl)-1H-imidazol-2-yl)pyrrolidin-1-yl)-2-oxo-1-(tetrahydro-2H-pyran-4-yl) ethylcarbamate (0.483 g, 80%). MS (ESI) m/z 583.333 [M+H]+.

Example AN

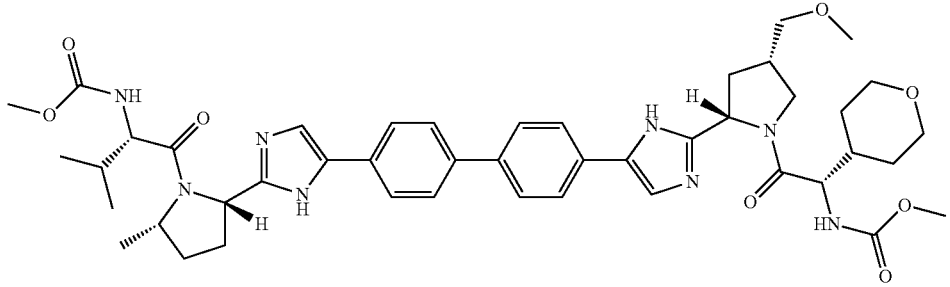

methyl [(1S)-2-[(2S,4S)-2-[5-(4'-{2-[(2S,5S)-1-{(2S)-2-[(methoxycarbonyl)amino]-3-methylbutanoyl}-5-methylpyrrolidin-2-yl]-1H-imidazol-5-yl}biphenyl-4-yl)-1H-imidazol-2-yl]-4-(methoxymethyl)pyrrolidin-1-yl]-2-oxo-1-(tetrahydro-2H-pyran-4-yl)ethyl]carbamate Methyl [(1S)-2-[(2S,4S)-2-[5-(4'-{2-[(2S,5S)-1-{(2S)-2-[(methoxycarbonyl)-amino]-3-methylbutanoyl}-5-methylpyrrolidin-2-yl]-1H-imidazol-5-yl}biphenyl-4-yl)-1H-imidazol-2-yl]-4-(methoxymethyl)pyrrolidin-1-yl]-2-oxo-1-(tetrahydro-2H-pyran-4-yl)ethyl]carbamate Methyl [(1S)-2-[(2S,4S)-2-[5-(4'-{2-[(2S,5S)-1-{(2S)-2-[(methoxycarbonyl)amino]-3-methylbutanoyl}-5-methylpyrrolidin-2-yl]-1H-imidazol-5-yl}biphenyl-4-yl)-1H-imidazol-2-yl]-4-(methoxymethyl)pyrrolidin-1-yl]-2-oxo-1-(tetrahydro-2H-pyran-4-yl)ethyl]carbamate was prepared following Example AC, substituting methyl (S)-2-((2S,4S)-4-(methoxymethyl)-2-(5-(4-(4,4,5,5-tetramethyl-1,3,2-dioxaborolan-2-yl)phenyl)-1H-imidazol-2-yl)pyrrolidin-1-yl)-2-oxo-1-(tetrahydro-2H-pyran-4-yl)ethylcarbamate for (2R,4S)-tert-butyl 4-(methoxymethyl)-2-(5-(4-(4,4,5,5-tetramethyl-1,3,2-dioxaborolan-2-yl)phenyl)-1H-imidazol-2-yl)pyrrolidine-1-carboxylate for (2S,3R)-3-methoxy-2-(methoxycarbonylamino)butanoic acid (0.150 g). $^1$H NMR (400 MHz, Methanol-$d_4$) δ 7.83 (d, J=7.9 Hz, 1H), 7.78-7.55 (m, 8H), 7.45-7.24 (m, 3H), 5.13-5.01 (m, 2H), 4.56 (s, 2H), 4.35-4.14 (m, 3H), 4.07 (d, 1H), 3.95-3.82 (m, 2H), 3.64 (s, 2H), 3.63 (s, 3H), 3.60-3.46 (m, 3H), 3.36 (s, 3H), 2.82-2.37 (m, 4H), 2.38-1.77 (m, 7H), 1.64-1.50 (m, 2H), 1.47 (d, 2H), 1.44-1.12 (m, 4H), 1.03 (s, 2H), 0.99 (d, 1H), 0.95 (d, 2H), 0.89-0.74 (m, 2H). MS (ESI) m/z 839.87 [M+H]+.

Using procedures similar to those described herein the following compounds of the invention can also be prepared:

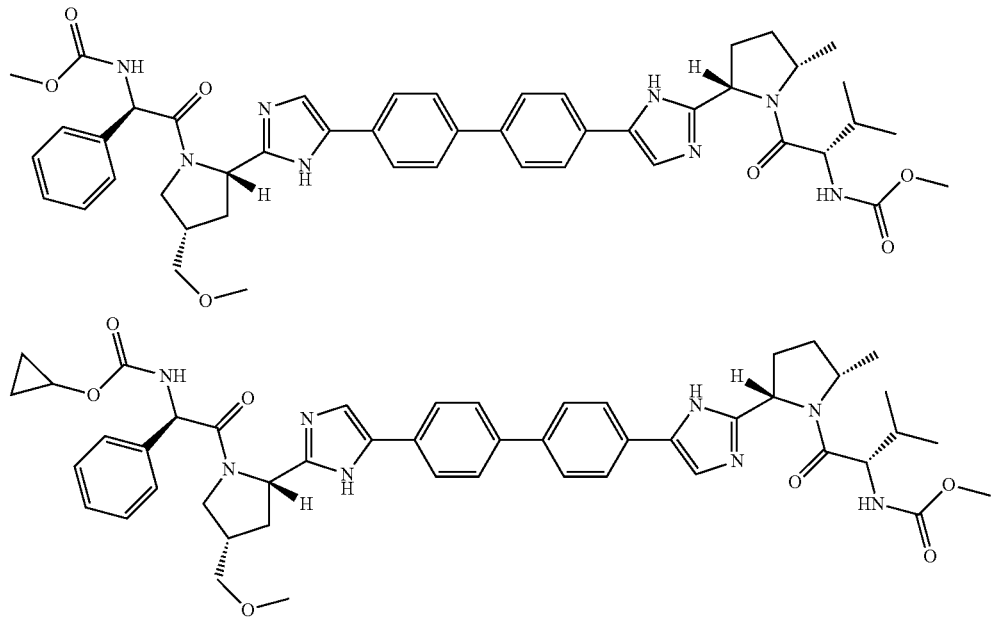

-continued
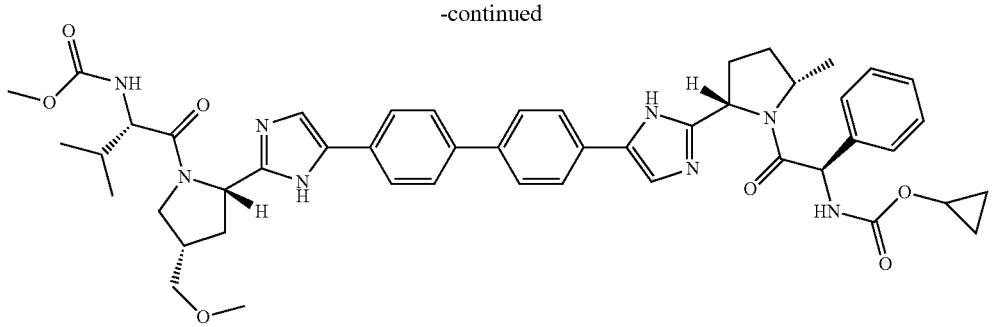
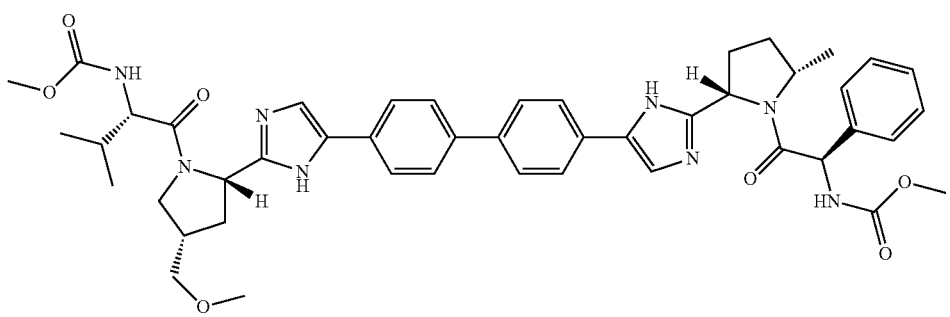
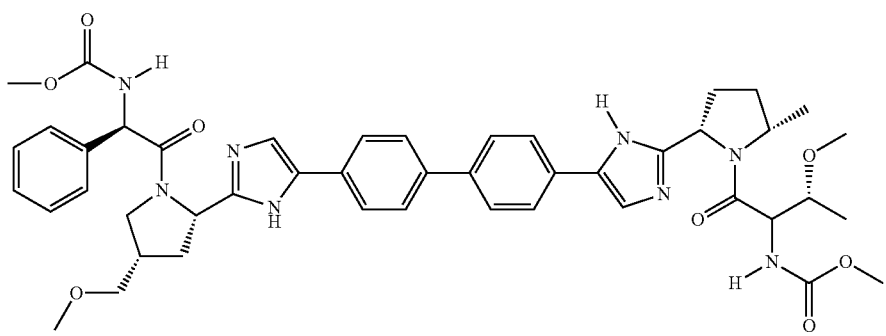
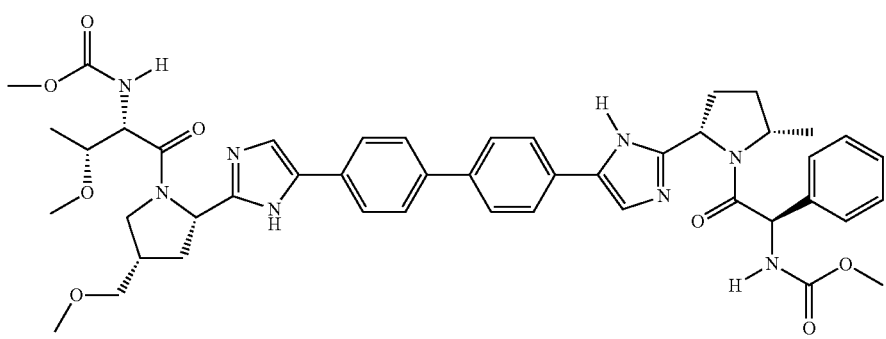
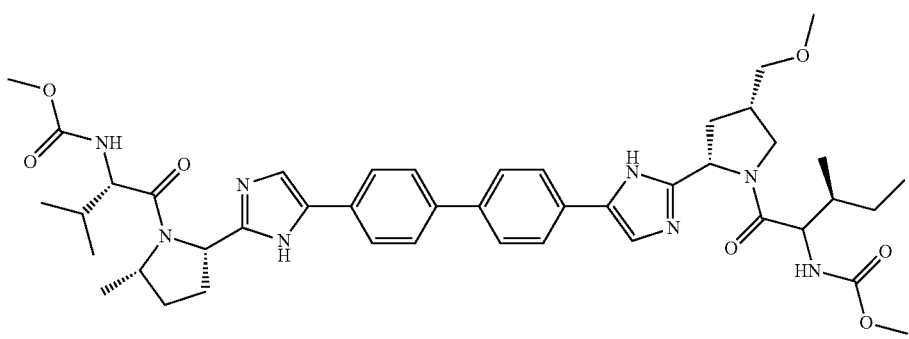

-continued
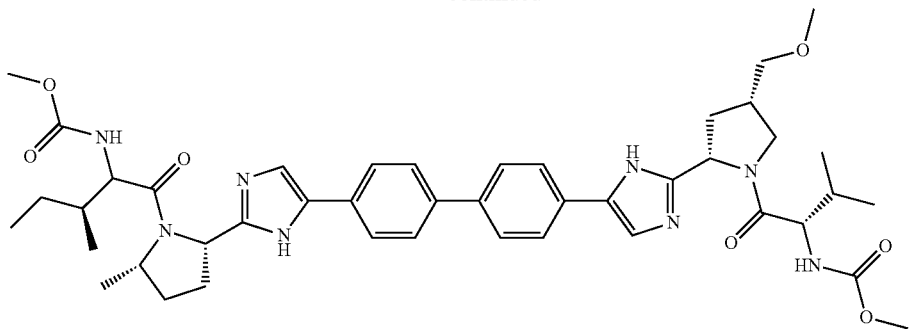
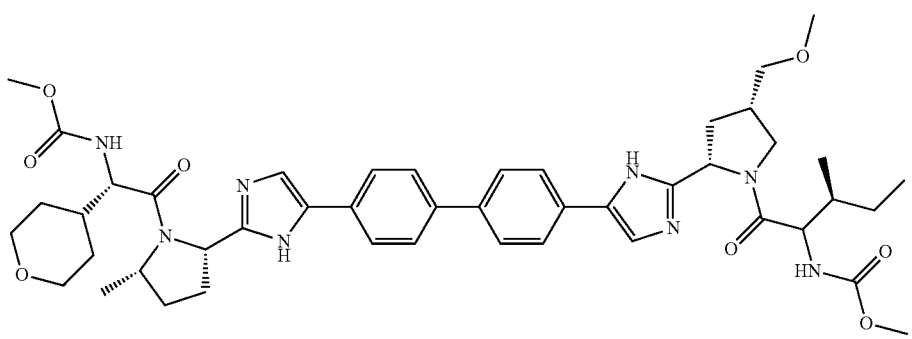
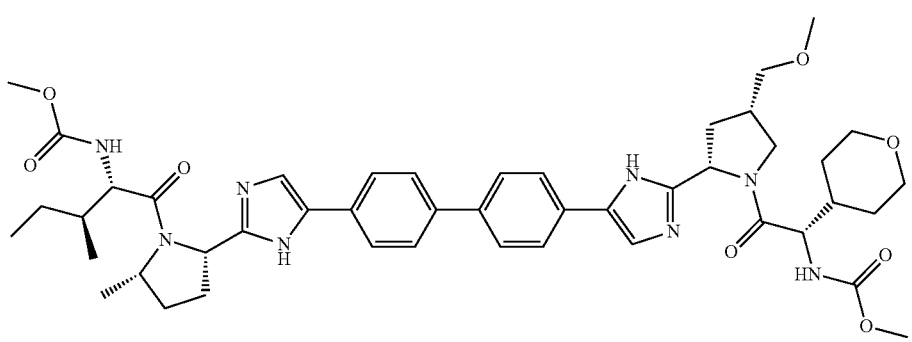
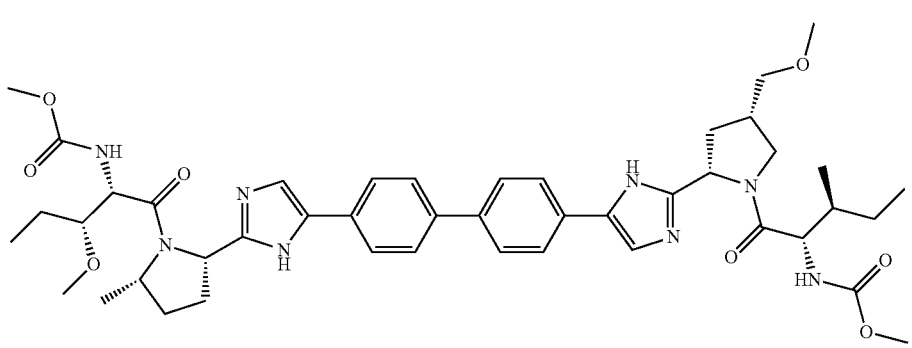
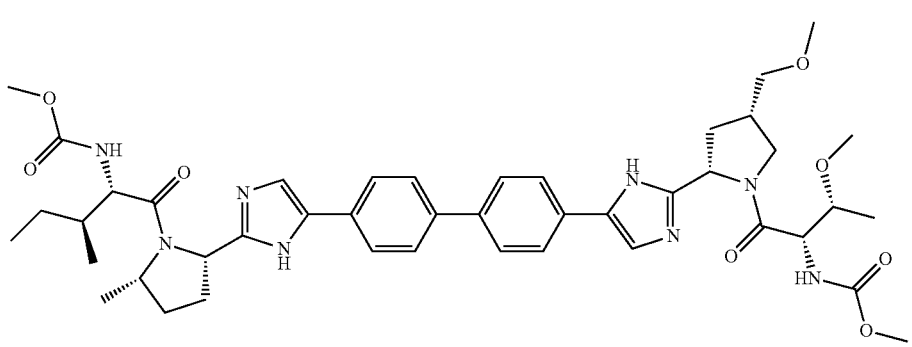

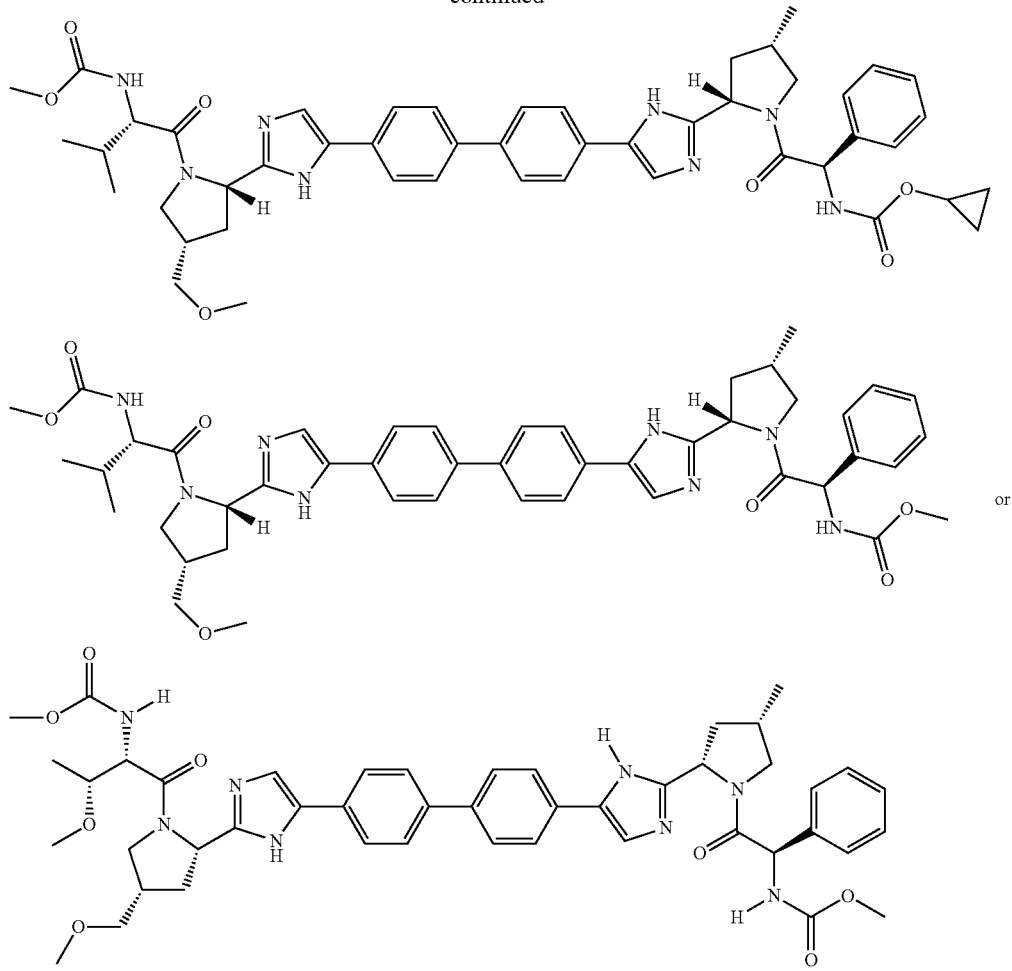

or a pharmaceutically acceptable salt thereof.

BIOLOGICAL ASSAYS

Evaluation of Cell-Based Anti-HCV Activity:

Antiviral potency ($EC_{50}$) was determined using a *Renilla luciferase* (RLuc)-based HCV replicon reporter assay. To perform the assay for genotype 1 and 2a JFH-1, stable HCV 1a RLuc replicon cells (harboring a dicistronic genotype 1a H77 replicon that encodes a RLuc reporter), stable HCV 1b RLuc replicon cells (harboring a dicistronic genotype 1b Con1 replicon that encodes a RLuc reporter), or stable HCV 2a JFH-1 Rluc replicon cells (harboring a dicistronic genotype 2a JFH-1 replicon that encodes a RLuc reporter; with L31 present in NS5A) were dispensed into 384-well plates for $EC_{50}$ assays. To perform the assay for genotype 2a (with M31 present in NS5A) or 2b, NS5A chimeric genotype 2a JFH-1 replicons that encodes a RLuc-Neo reporter and either genotype 2a J6 strain NS5A gene or genotype 2b MD2b-1 strain NS5A gene (both with M31 present) respectively, were either transiently transfected (t) into Huh-Lunet cells or were established as stably replicating replicon cells (s). Either cells were dispensed into 384-well plates for $EC_{50}$ assays. To perform the assay for genotype 3 and 4, NS5A chimeric genotype 1b Con1 replicons that encodes a Pi-RLuc reporter and either genotype 3a S52 strain NS5A gene or genotype 4a ED43 strain NS5A gene respectively, were transiently transfected (t) into Huh-Lunet cells, which were subsequently dispensed into 384-well plates. Alternatively, stable HCV 3a RLuc replicon cells (s) (harboring a dicistronic genotype 3a S52 replicon that encodes an RLuc reporter), or stable HCV 4a RLuc replicon cells (s) (harboring a dicistronic genotype 4a ED43 replicon that encodes a RLuc reporter) were established in Huh-7-derived cells and dispensed into 384-well plates for $EC_{50}$ assays. Compounds were dissolved in DMSO at a concentration of 10 mM and diluted in DMSO either manually or using an automated pipeting instrument. Serially 3-fold diluted compounds were either manually mixed with cell culture media and added to the seeded cells or directly added to the cells using an automated instrument. DMSO was used as a negative (solvent; no inhibition) control, and the protease inhibitor ITMN-191 was included at a concentration >100× $EC_{50}$ as a positive control. 72 hours later, cells were lysed and *Renilla luciferase* activity quantified as recommended by the manufacturer (Promega-Madison, Wis.). Non-linear regression was performed to calculate $EC_{50}$ values.

To determine the antiviral potency ($EC_{50}$) against resistance mutants, resistance mutations, including M28T, Q30R, Q30H, L31M, and Y93C in genotype 1a NS5A and Y93H in genotype 1b NS5A, were introduced individually into either 1a Pi-Rluc or 1b Pi-Rluc replicons by site directed mutagenesis. Replicon RNA of each resistant mutant was transiently transfected into Huh-7-derived cured-51 cells and antiviral potency was determined on these transfected cells as described above.

| # | Example No. | 1b (nM) | 1a | 1a Q30R | 2a JFH | 2a J6 (t) | 2b (s) | 3a (s) | 4a (s) | 1a (nM) | 1a Q30R (nM) | 2a JFH (nM) | 2a J6 (t) (nM) | 2b (s) (nM) | 3a (s) (nM) | 4a (s) (nM) |
|---|---|---|---|---|---|---|---|---|---|---|---|---|---|---|---|---|
| 1 | AH | 0.040 | D | | D | | B | B | D | 0.037 | | 0.066 | | 7.298 | 36.533 | 0.020 |
| 2 | AI | 0.028 | D | | D | | B | B | D | 0.034 | | 0.075 | | 5.080 | 40.753 | 0.018 |
| 3 | AG | 0.019 | D | | D | | B | B | D | 0.022 | | 0.050 | | 2.565 | 17.616 | 0.011 |
| 4 | AF | 0.055 | D | | D | | B | B | D | 0.045 | | 0.031 | | 1.048 | 3.196 | 0.022 |
| 5 | AE | 0.077 | D | | D | | B | B | D | 0.062 | | 0.047 | | 1.871 | 8.368 | 0.033 |
| 6 | AD | 0.106 | D | | D | | B | B | D | 0.064 | | 0.041 | | 2.238 | 5.666 | 0.039 |
| 7 | AC | 0.127 | D | C | D | | B | B | | 0.092 | 0.224 | 0.038 | | 4.139 | 3.924 | |
| 8 | AN | 0.065 | D | | D | C | B | B | D | 0.037 | | 0.027 | 0.207 | 2.138 | 2.188 | 0.035 |
| 9 | AL | 0.074 | D | | D | D | B | B | D | 0.052 | | 0.035 | 0.084 | 2.170 | 2.140 | 0.040 |
| 10 | AJ | 0.384 | C | | D | C | C | B | C | 0.186 | | 0.079 | 0.155 | 0.672 | 1.342 | 0.133 |
Activity Ranges: A ≥ 44 nM, B = 1 nM-43.999 nM, C = 0.1 nM-0.999 nM, D < 0.1 nM.
We claim:
1. A compound selected from:
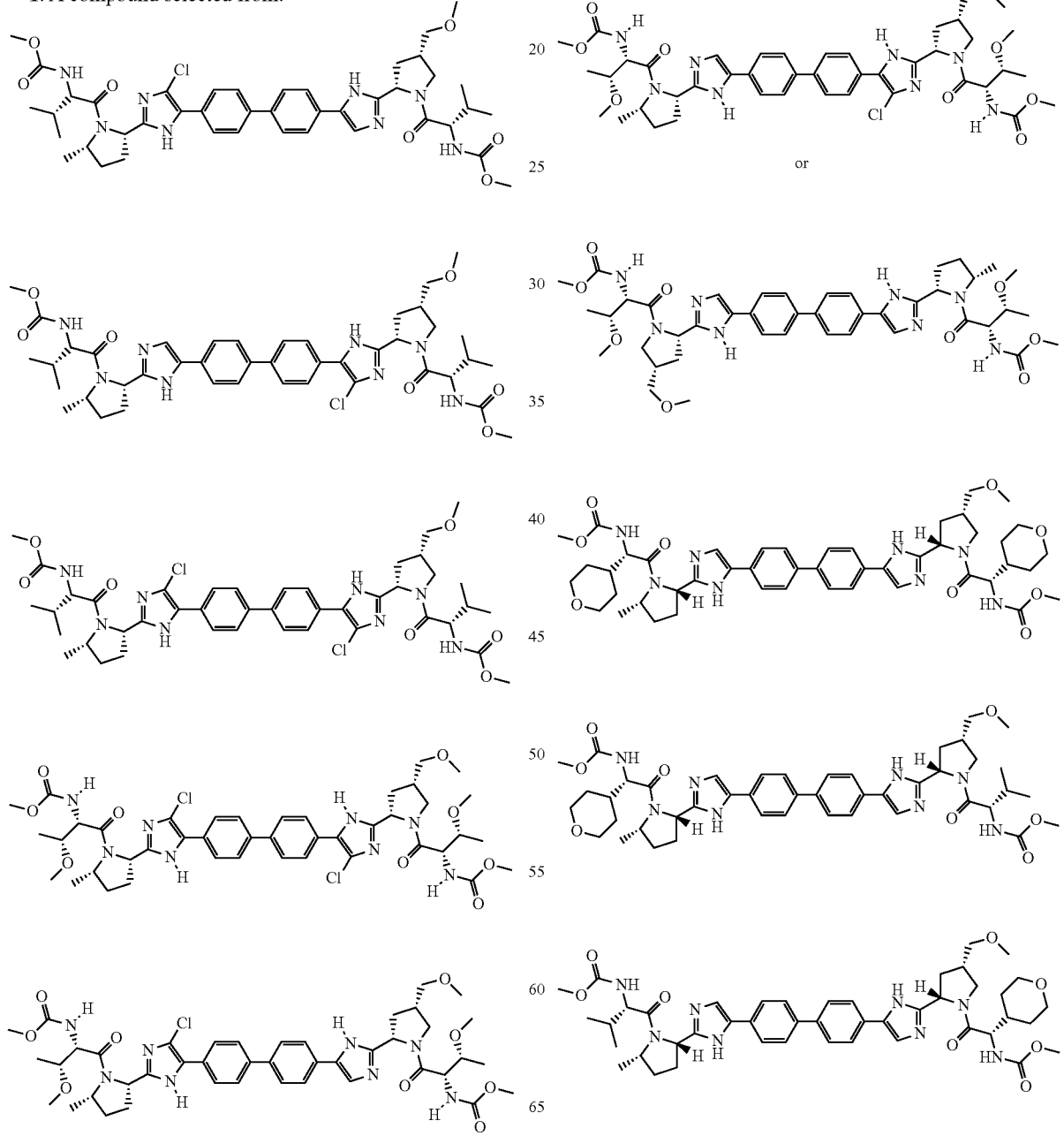
or a pharmaceutically acceptable salt or prodrug thereof.

2. A compound selected from:
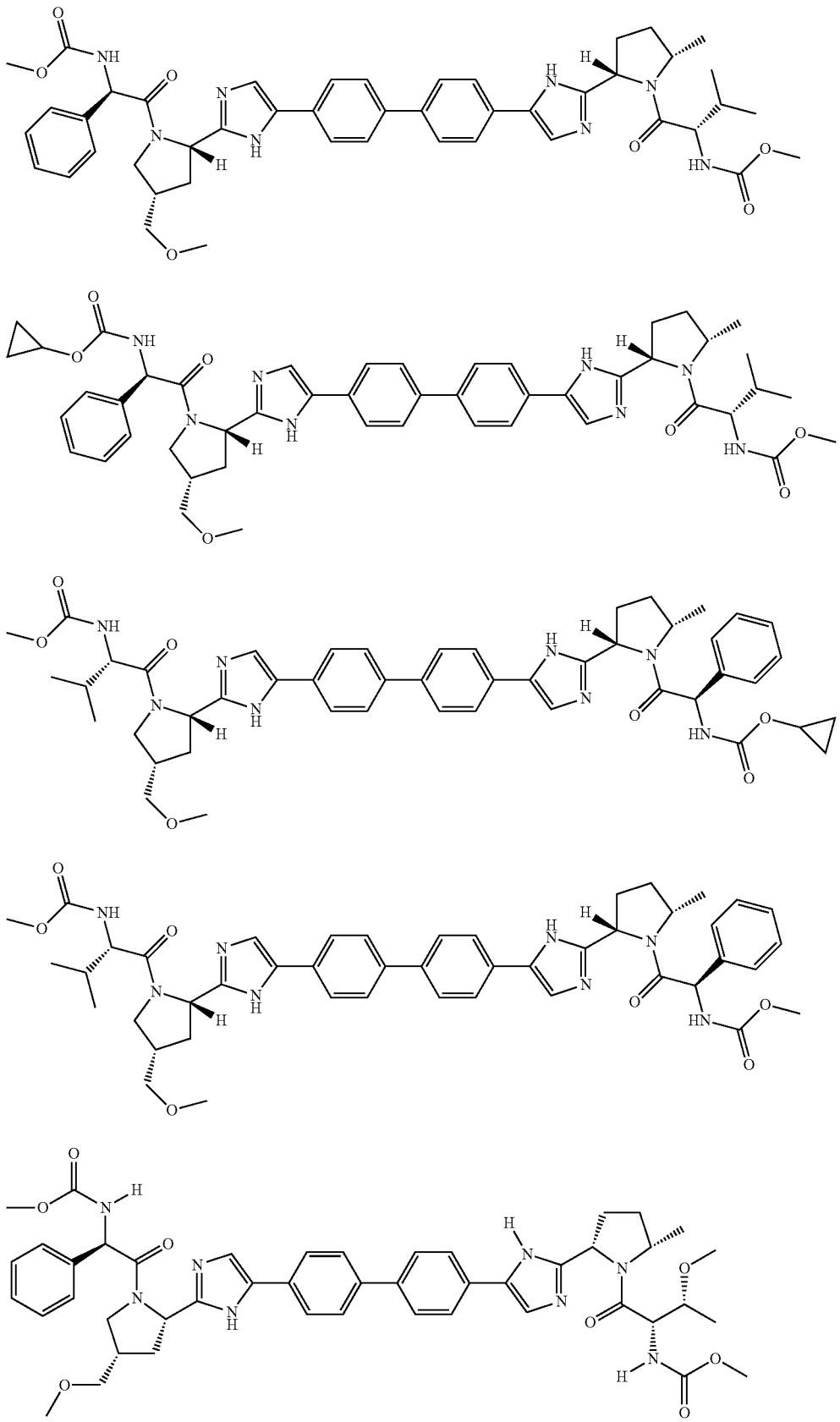

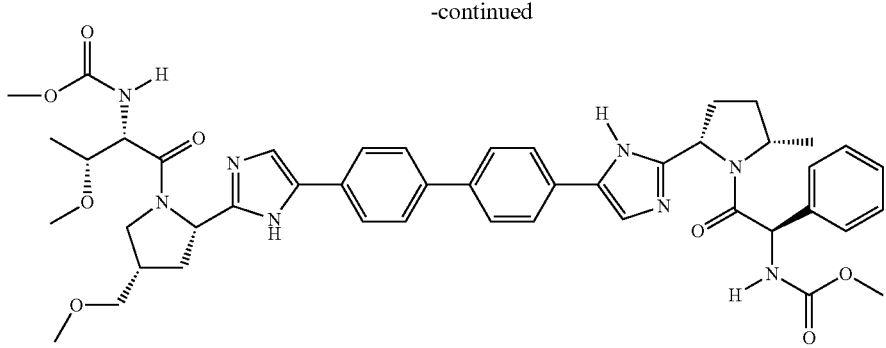
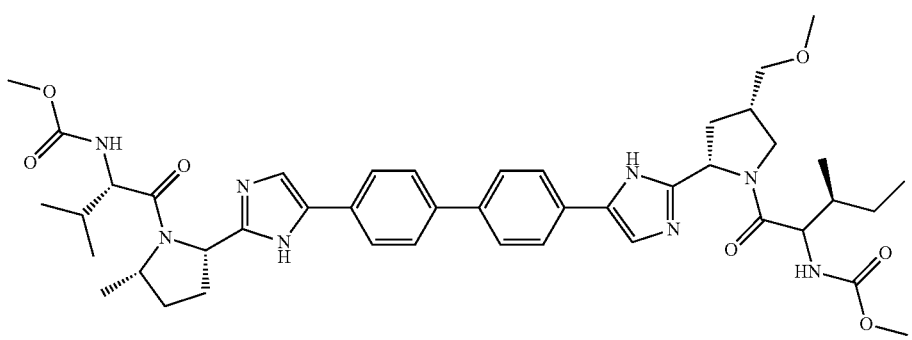
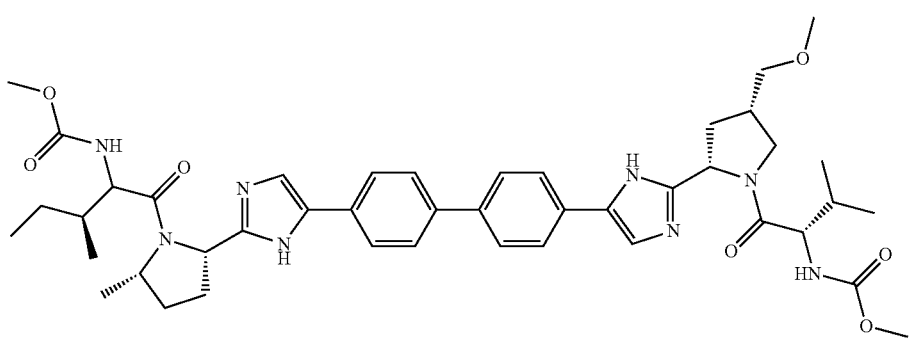
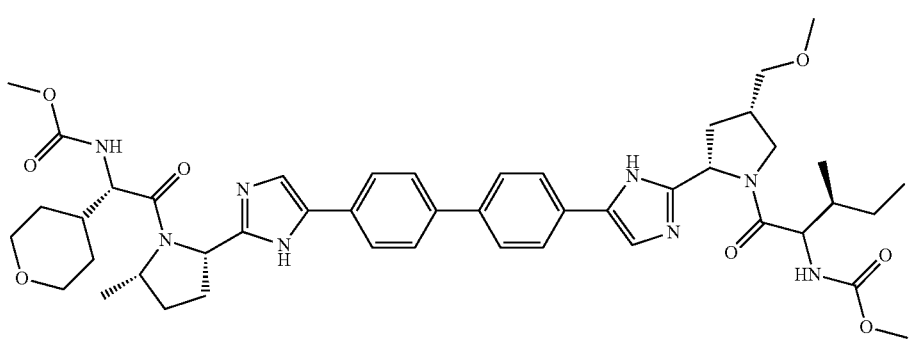
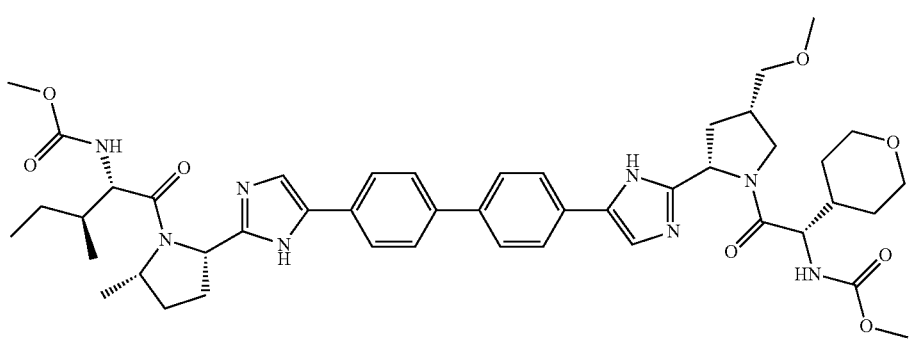

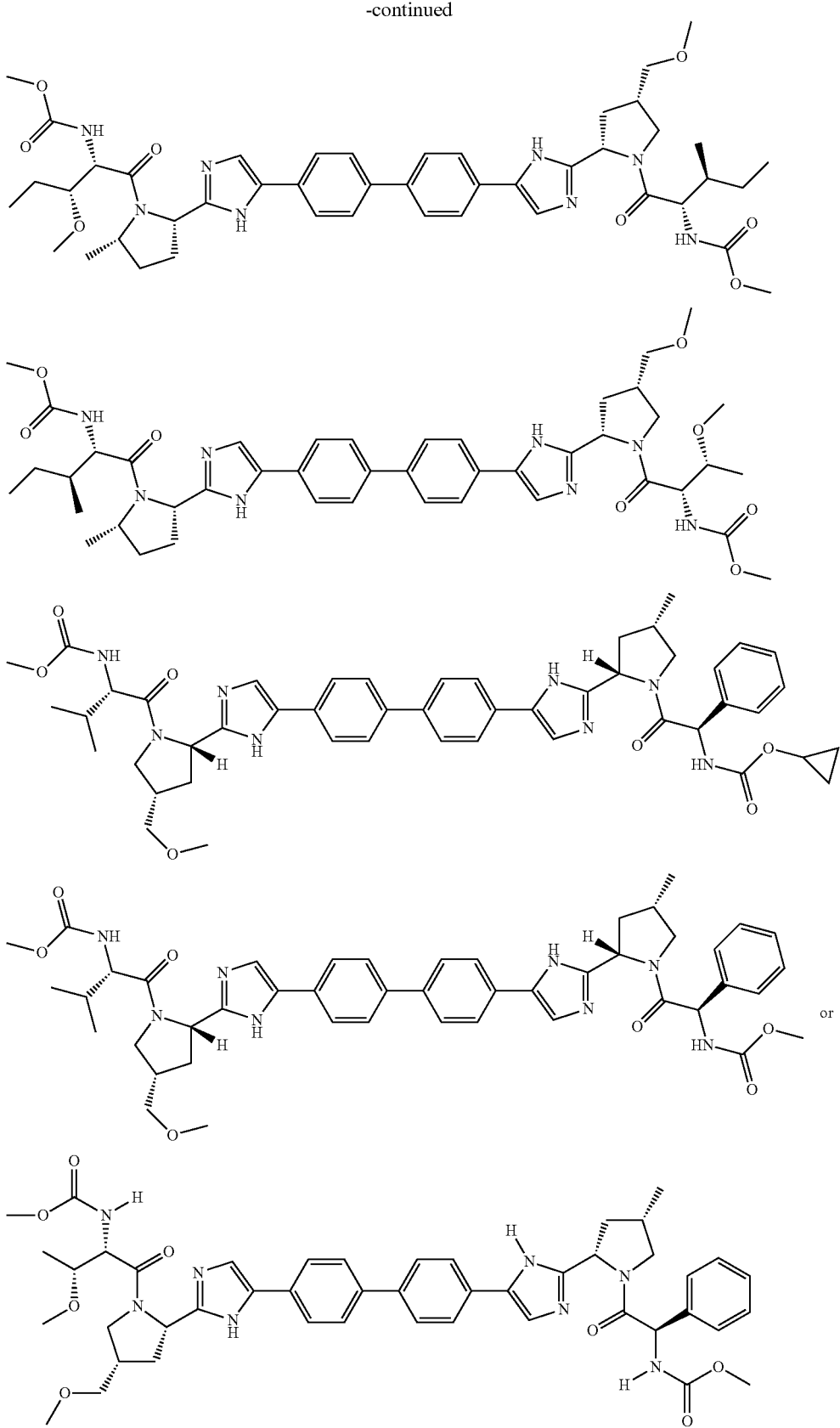
or a pharmaceutically acceptable salt or prodrug thereof.

3. A pharmaceutical composition comprising the compound as described in claim 1 or a pharmaceutically acceptable salt thereof, and at least one pharmaceutically acceptable carrier.

4. The pharmaceutical composition of claim 3, further comprising at least one additional therapeutic agent for treating HCV.

5. The pharmaceutical composition of claim 4, wherein said additional therapeutic agent is selected from ribavirin, an NS3 protease inhibitor, a nucleoside or nucleotide inhibitor of HCV NS5B polymerase, an alpha-glucosidase 1 inhibitor, a hepatoprotectant, a non-nucleoside inhibitor of HCV polymerase, or combinations thereof.

6. The pharmaceutical composition according to claim 3, further comprising a nucleoside or nucleotide inhibitor of HCV NS5B polymerase.

7. The pharmaceutical composition according to claim 6, wherein said nucleoside or nucleotide inhibitor of HCV NS5B polymerase is selected from ribavirin, viramidine, levovirin, a L-nucleoside, or isatoribine.

8. A pharmaceutical composition comprising a compound as in claim 1, at least one nucleoside or nucleotide inhibitor of HCV NS5B polymerase, and at least one pharmaceutically acceptable carrier.

9. The pharmaceutical composition according to claim 8, further comprising an interferon, a pegylated interferon, ribavirin or combinations thereof.

10. The pharmaceutical composition of claim 8, wherein the nucleoside or nucleotide inhibitor of HCV NS5B polymerase is sofosbuvir.

11. A pharmaceutical composition comprising a compound as in claim 1, at least one NS3 protease inhibitor, and at least one pharmaceutically acceptable carrier.

12. The pharmaceutical composition according to claim 11, further comprising sofosbuvir.

13. A method of treating hepatitis C, said method comprising administering to a human patient in need thereof a pharmaceutical composition which comprises a therapeutically effective amount of the compound as described in claim 1 or a pharmaceutically acceptable salt, or prodrug thereof.

14. The method according to claim 13, further comprising administering to the patient an interferon or pegylated interferon.

15. The method of claim 13, further comprising administering to the patient ribavirin.

16. A pharmaceutical composition comprising the compound as described in claim 2 or a pharmaceutically acceptable salt thereof, and at least one pharmaceutically acceptable carrier.

17. The pharmaceutical composition of claim 16, further comprising at least one additional therapeutic agent for treating HCV.

18. The pharmaceutical composition of claim 17, wherein said additional therapeutic agent is selected from ribavirin, an NS3 protease inhibitor, a nucleoside or nucleotide inhibitor of HCV NS5B polymerase, an alpha-glucosidase 1 inhibitor, a hepatoprotectant, a non-nucleoside inhibitor of HCV polymerase, or combinations thereof.

19. The pharmaceutical composition according to claim 16, further comprising a nucleoside or nucleotide inhibitor of HCV NS5B polymerase.

20. The pharmaceutical composition according to claim 19, wherein said nucleoside or nucleotide inhibitor of HCV NS5B polymerase is selected from ribavirin, viramidine, levovirin, a L-nucleoside, or isatoribine.

21. A pharmaceutical composition comprising a compound as in claim 2, at least one nucleoside or nucleotide inhibitor of HCV NS5B polymerase, and at least one pharmaceutically acceptable carrier.

22. The pharmaceutical composition according to claim 21, further comprising an interferon, a pegylated interferon, ribavirin or combinations thereof.

23. The pharmaceutical composition of claim 21, wherein the nucleoside or nucleotide inhibitor of HCV NS5B polymerase is sofosbuvir.

24. A pharmaceutical composition comprising a compound as in claim 2, at least one NS3 protease inhibitor, and at least one pharmaceutically acceptable carrier.

25. The pharmaceutical composition according to claim 24, further comprising sofosbuvir.

26. A method of treating hepatitis C, said method comprising administering to a human patient in need thereof a pharmaceutical composition which comprises a therapeutically effective amount of the compound as described in claim 2 or a pharmaceutically acceptable salt, or prodrug thereof.

27. The method according to claim 26, further comprising administering to the patient an interferon or pegylated interferon.

28. The method of claim 26, further comprising administering to the patient ribavirin.

* * * * *